(12) United States Patent
Zubok et al.

(10) Patent No.: US 8,109,979 B2
(45) Date of Patent: Feb. 7, 2012

(54) INSTRUMENTATION AND METHODS FOR USE IN IMPLANTING A CERVICAL DISC REPLACEMENT DEVICE

(75) Inventors: Rafail Zubok, Midland Park, NJ (US); Michael W. Dudasik, Nutley, NJ (US); Joseph P. Errico, Green Brook, NJ (US)

(73) Assignee: SpineCore, Inc., Allendale, NJ (US)

( * ) Notice: Subject to any disclaimer, the term of this patent is extended or adjusted under 35 U.S.C. 154(b) by 0 days.

(21) Appl. No.: 12/634,182

(22) Filed: Dec. 9, 2009

(65) Prior Publication Data

US 2010/0087870 A1    Apr. 8, 2010

Related U.S. Application Data

(60) Division of application No. 10/781,505, filed on Feb. 18, 2004, now Pat. No. 7,648,511, which is a continuation of application No. 10/688,632, filed on Oct. 17, 2003, now Pat. No. 6,896,676, which is a continuation-in-part of application No. 10/382,702, filed on Mar. 6, 2003, now Pat. No. 6,908,484.

(51) Int. Cl.
*A61B 17/70* (2006.01)

(52) U.S. Cl. .......... 606/279; 606/96; 623/17.11

(58) Field of Classification Search .......... 606/96, 606/281, 279; 623/17.11–17.16
See application file for complete search history.

(56) References Cited

U.S. PATENT DOCUMENTS

| | | |
|---|---|---|
| 916,421 A | 3/1909 | Crittenden |
| 2,193,122 A | 3/1940 | Crabbs |
| 2,669,896 A | 2/1954 | Clough |
| 2,774,350 A | 12/1956 | Cleveland, Jr. |
| 3,086,208 A | 4/1963 | Eby |
| 3,278,107 A | 10/1966 | Rygg |
| 3,486,505 A | 12/1969 | Morrison |
| 3,604,487 A | 9/1971 | Gilbert |
| 3,867,728 A | 2/1975 | Stubstad et al. |
| 3,872,519 A | 3/1975 | Giannestras et al. |
| 4,021,864 A | 5/1977 | Waugh |
| 4,105,407 A | 8/1978 | Sanderson |
| 4,217,902 A | 8/1980 | March |
| 4,263,903 A | 4/1981 | Griggs |
| 4,296,751 A | 10/1981 | Blake, III et al. |
| 4,303,001 A | 12/1981 | Trungold |
| 4,309,777 A | 1/1982 | Patil |
| 4,457,484 A | 7/1984 | Hameister |

(Continued)

FOREIGN PATENT DOCUMENTS

DE    3023492 A1    2/1982

(Continued)

*Primary Examiner* — Pedro Philogene
(74) *Attorney, Agent, or Firm* — Lerner, David, Littenberg, Krumholtz & Mentlik, LLP

(57) ABSTRACT

Instrumentation for implanting a cervical disc replacement device includes cervical disc replacement trials for determining the appropriate size of replacement device to be implanted, an insertion plate for maintaining the elements of the replacement device in fixed relation to one another for simultaneous manipulation, an insertion handle for attachment to the insertion plate for manipulation of the elements, an insertion pusher for releasing the insertion handle from the insertion plate, a drill guide that cooperates with the insertion plate to guide the drilling of tap holes for bone screws to be placed through bone screw holes in the flanges of the replacement device, clips that are applied to the flanges after placement of the bone screws to resist screw backout, and a clip applicator for applying the clips to the flanges.

20 Claims, 17 Drawing Sheets

U.S. PATENT DOCUMENTS

| | | |
|---|---|---|
| 4,528,980 A | 7/1985 | Kenna |
| 4,531,517 A | 7/1985 | Forte et al. |
| 4,566,466 A | 1/1986 | Ripple et al. |
| 4,605,417 A | 8/1986 | Fleischauer |
| 4,733,657 A | 3/1988 | Kluger |
| 4,759,766 A | 7/1988 | Buettner-Janz et al. |
| 4,759,769 A | 7/1988 | Hedman et al. |
| 4,874,314 A | 10/1989 | Fleer et al. |
| 4,917,704 A | 4/1990 | Frey et al. |
| 4,932,969 A | 6/1990 | Frey et al. |
| 4,955,908 A | 9/1990 | Frey et al. |
| 4,969,907 A | 11/1990 | Koch et al. |
| 4,997,432 A | 3/1991 | Keller |
| 5,002,576 A | 3/1991 | Fuhrmann et al. |
| 5,030,219 A | 7/1991 | Matsen, III et al. |
| 5,034,254 A | 7/1991 | Cologna et al. |
| 5,112,178 A | 5/1992 | Overhues et al. |
| 5,122,130 A | 6/1992 | Keller |
| 5,192,327 A | 3/1993 | Brantigan |
| 5,236,460 A | 8/1993 | Barber |
| 5,246,458 A | 9/1993 | Graham |
| 5,258,007 A | 11/1993 | Spetzler et al. |
| 5,258,031 A | 11/1993 | Salib et al. |
| 5,269,790 A | 12/1993 | Funatsu |
| 5,306,308 A | 4/1994 | Gross et al. |
| 5,314,477 A | 5/1994 | Marnay |
| 5,364,399 A | 11/1994 | Lowery et al. |
| 5,370,697 A | 12/1994 | Baumgartner |
| 5,376,120 A | 12/1994 | Sarver et al. |
| 5,401,269 A | 3/1995 | Buttner-Janz et al. |
| 5,405,400 A | 4/1995 | Linscheid et al. |
| 5,425,773 A | 6/1995 | Boyd et al. |
| 5,443,514 A | 8/1995 | Steffee |
| 5,458,641 A | 10/1995 | Ramirez Jimenez |
| 5,458,642 A | 10/1995 | Beer et al. |
| 5,507,816 A | 4/1996 | Bullivant |
| 5,514,180 A | 5/1996 | Heggeness et al. |
| 5,522,900 A | 6/1996 | Hollister |
| 5,534,029 A | 7/1996 | Shima |
| 5,548,642 A | 8/1996 | Diethorn |
| 5,549,690 A | 8/1996 | Hollister et al. |
| 5,556,431 A | 9/1996 | Buttner-Janz |
| 5,556,432 A | 9/1996 | Kubein-Meesenburg et al. |
| 5,562,736 A | 10/1996 | Ray et al. |
| 5,562,738 A | 10/1996 | Boyd et al. |
| 5,593,456 A | 1/1997 | Merlette |
| 5,599,279 A | 2/1997 | Slotman et al. |
| 5,645,605 A | 7/1997 | Klawitter |
| 5,653,762 A | 8/1997 | Pisharodi |
| 5,674,296 A | 10/1997 | Bryan et al. |
| 5,676,701 A | 10/1997 | Yuan et al. |
| 5,676,702 A | 10/1997 | Ratron |
| 5,683,464 A | 11/1997 | Wagner et al. |
| 5,683,465 A | 11/1997 | Shinn et al. |
| 5,720,751 A | 2/1998 | Jackson |
| 5,732,992 A | 3/1998 | Mauldin |
| 5,733,290 A | 3/1998 | McCue et al. |
| 5,755,796 A | 5/1998 | Ibo et al. |
| 5,769,856 A | 6/1998 | Dong et al. |
| 5,776,198 A | 7/1998 | Rabbe et al. |
| 5,782,830 A | 7/1998 | Farris |
| 5,782,832 A | 7/1998 | Larsen et al. |
| 5,827,328 A | 10/1998 | Buttermann |
| 5,860,990 A | 1/1999 | Nobles et al. |
| 5,865,846 A | 2/1999 | Bryan et al. |
| 5,888,223 A | 3/1999 | Bray, Jr. |
| 5,888,226 A | 3/1999 | Rogozinski |
| 5,893,889 A | 4/1999 | Harrington |
| 5,895,428 A | 4/1999 | Berry |
| 5,899,941 A | 5/1999 | Nishijima et al. |
| 5,910,141 A | 6/1999 | Morrison et al. |
| 5,916,267 A | 6/1999 | Tienboon |
| 5,926,685 A | 7/1999 | Krebs et al. |
| 5,928,284 A | 7/1999 | Mehdizadeh |
| 5,976,186 A | 11/1999 | Bao et al. |
| 5,983,889 A | 11/1999 | Thomas |
| 5,989,291 A | 11/1999 | Ralph et al. |
| 5,989,294 A | 11/1999 | Marlow |
| 6,001,030 A | 12/1999 | Delaney |
| 6,001,130 A | 12/1999 | Bryan et al. |
| 6,019,792 A | 2/2000 | Cauthen |
| 6,039,763 A | 3/2000 | Shelokov |
| 6,050,999 A | 4/2000 | Paraschac et al. |
| 6,051,751 A | 4/2000 | Sioshansi et al. |
| 6,063,121 A | 5/2000 | Xavier et al. |
| 6,066,174 A | 5/2000 | Farris |
| 6,066,175 A | 5/2000 | Henderson et al. |
| 6,080,155 A | 6/2000 | Michelson |
| 6,093,205 A | 7/2000 | McLeod et al. |
| 6,093,207 A | 7/2000 | Pisharodi |
| 6,096,080 A | 8/2000 | Nicholson et al. |
| 6,106,557 A | 8/2000 | Robioneck et al. |
| 6,111,222 A | 8/2000 | Hattori |
| 6,113,602 A | 9/2000 | Sand |
| 6,113,637 A * | 9/2000 | Gill et al. ................... 623/17.15 |
| 6,113,638 A | 9/2000 | Williams et al. |
| 6,113,639 A | 9/2000 | Ray et al. |
| 6,136,031 A | 10/2000 | Middleton |
| 6,139,550 A | 10/2000 | Michelson |
| 6,143,012 A | 11/2000 | Gausepohl |
| 6,146,421 A | 11/2000 | Gordon et al. |
| 6,156,067 A | 12/2000 | Bryan et al. |
| 6,159,215 A | 12/2000 | Urbahns et al. |
| 6,162,252 A | 12/2000 | Kuras et al. |
| 6,174,311 B1 | 1/2001 | Branch et al. |
| 6,179,873 B1 | 1/2001 | Zientek |
| 6,179,874 B1 | 1/2001 | Cauthen |
| 6,190,413 B1 | 2/2001 | Sutcliffe |
| 6,190,414 B1 | 2/2001 | Young et al. |
| 6,193,757 B1 | 2/2001 | Foley et al. |
| 6,213,055 B1 | 4/2001 | Willinger et al. |
| 6,214,005 B1 | 4/2001 | Benzel et al. |
| 6,214,049 B1 | 4/2001 | Gayer et al. |
| 6,217,615 B1 | 4/2001 | Sioshansi et al. |
| 6,224,607 B1 | 5/2001 | Michelson |
| 6,228,023 B1 | 5/2001 | Zaslavsky et al. |
| 6,228,118 B1 | 5/2001 | Gordon |
| 6,231,609 B1 | 5/2001 | Mehdizadeh |
| 6,235,034 B1 | 5/2001 | Bray |
| 6,235,059 B1 | 5/2001 | Benezech et al. |
| 6,235,060 B1 | 5/2001 | Kubein-Meesenburg et al. |
| 6,241,732 B1 | 6/2001 | Overaker et al. |
| 6,241,769 B1 | 6/2001 | Nicholson et al. |
| 6,261,293 B1 | 7/2001 | Nicholson et al. |
| 6,261,296 B1 | 7/2001 | Aebi et al. |
| 6,261,324 B1 | 7/2001 | Merlette |
| 6,277,149 B1 | 8/2001 | Boyle et al. |
| 6,280,458 B1 | 8/2001 | Boche et al. |
| 6,296,647 B1 | 10/2001 | Robioneck et al. |
| 6,296,665 B1 | 10/2001 | Strnad et al. |
| 6,319,257 B1 | 11/2001 | Carignan et al. |
| 6,325,828 B1 | 12/2001 | Dennis et al. |
| 6,332,887 B1 | 12/2001 | Knox |
| 6,342,057 B1 | 1/2002 | Brace et al. |
| 6,348,071 B1 | 2/2002 | Steffee et al. |
| 6,368,350 B1 | 4/2002 | Erickson et al. |
| 6,375,682 B1 | 4/2002 | Fleischmann et al. |
| 6,395,030 B1 | 5/2002 | Songer et al. |
| 6,395,032 B1 | 5/2002 | Gauchet |
| 6,395,035 B2 | 5/2002 | Bresina et al. |
| 6,398,815 B1 | 6/2002 | Pope et al. |
| 6,413,259 B1 | 7/2002 | Lyons et al. |
| 6,416,551 B1 | 7/2002 | Keller |
| 6,425,920 B1 | 7/2002 | Hamada |
| 6,428,544 B1 | 8/2002 | Ralph et al. |
| 6,432,106 B1 | 8/2002 | Fraser |
| 6,436,102 B1 | 8/2002 | Ralph et al. |
| 6,440,139 B2 | 8/2002 | Michelson |
| 6,440,168 B1 | 8/2002 | Cauthen |
| 6,447,547 B1 | 9/2002 | Michelson |
| 6,461,359 B1 | 10/2002 | Tribus et al. |
| 6,468,310 B1 | 10/2002 | Ralph et al. |
| 6,471,725 B1 | 10/2002 | Ralph et al. |
| 6,478,796 B2 | 11/2002 | Zucherman et al. |
| 6,478,800 B1 | 11/2002 | Fraser et al. |
| 6,478,801 B1 | 11/2002 | Ralph et al. |
| 6,488,710 B2 | 12/2002 | Besselink |

| Patent No. | Date | Inventor |
|---|---|---|
| 6,499,595 B1 | 12/2002 | Petricca |
| 6,517,580 B1 | 2/2003 | Ramadan et al. |
| 6,520,996 B1 | 2/2003 | Manasas et al. |
| 6,524,312 B2 | 2/2003 | Landry et al. |
| 6,527,320 B1 | 3/2003 | Gregg |
| 6,527,786 B1 | 3/2003 | Davis et al. |
| 6,527,804 B1 | 3/2003 | Gauchet et al. |
| 6,527,806 B2 | 3/2003 | Ralph et al. |
| 6,540,785 B1 | 4/2003 | Gill et al. |
| 6,554,864 B2 | 4/2003 | Ralph et al. |
| 6,562,047 B2 | 5/2003 | Ralph et al. |
| 6,562,073 B2 | 5/2003 | Foley |
| 6,572,653 B1 | 6/2003 | Simonson |
| 6,576,017 B2 | 6/2003 | Foley et al. |
| 6,579,290 B1 | 6/2003 | Hardcastle et al. |
| 6,579,320 B1 | 6/2003 | Gauchet et al. |
| 6,579,321 B1 | 6/2003 | Gordon et al. |
| 6,582,466 B1 | 6/2003 | Gauchet |
| 6,582,468 B1 | 6/2003 | Gauchet |
| 6,589,247 B2 | 7/2003 | McGahan et al. |
| 6,592,624 B1 | 7/2003 | Fraser et al. |
| 6,599,291 B1 | 7/2003 | Foley et al. |
| 6,602,292 B2 | 8/2003 | Burkinshaw |
| 6,607,558 B2 | 8/2003 | Kuras |
| 6,607,559 B2 | 8/2003 | Ralph et al. |
| 6,610,092 B2 | 8/2003 | Ralph et al. |
| 6,610,093 B1 | 8/2003 | Pisharodi |
| 6,623,525 B2 | 9/2003 | Ralph et al. |
| 6,632,091 B1 | 10/2003 | Cise et al. |
| 6,641,614 B1 | 11/2003 | Wagner et al. |
| 6,645,248 B2 | 11/2003 | Casutt |
| 6,645,249 B2 | 11/2003 | Ralph et al. |
| 6,652,233 B2 | 11/2003 | Otake |
| 6,652,525 B1 | 11/2003 | Assaker et al. |
| 6,652,533 B2 | 11/2003 | O'Neil |
| 6,666,866 B2 | 12/2003 | Martz et al. |
| 6,669,699 B2 | 12/2003 | Ralph et al. |
| 6,669,730 B2 | 12/2003 | Ralph et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,679,887 B2 | 1/2004 | Nicholson et al. |
| 6,679,915 B1 | 1/2004 | Cauthen |
| 6,682,562 B2 | 1/2004 | Viart et al. |
| 6,692,495 B1 | 2/2004 | Zacouto |
| 6,706,068 B2 | 3/2004 | Ferree |
| 6,709,439 B2 | 3/2004 | Rogers et al. |
| 6,712,825 B2 | 3/2004 | Aebi et al. |
| 6,716,245 B2 | 4/2004 | Pasquet et al. |
| 6,730,127 B2 | 5/2004 | Michelson |
| 6,740,118 B2 | 5/2004 | Eisermann et al. |
| 6,743,257 B2 | 6/2004 | Castro |
| 6,755,841 B2 | 6/2004 | Fraser et al. |
| 6,770,096 B2 | 8/2004 | Bolger et al. |
| 6,793,678 B2 | 9/2004 | Hawkins |
| 6,796,988 B2 | 9/2004 | Melkent et al. |
| 6,800,093 B2 | 10/2004 | Nicholson et al. |
| 6,827,743 B2 | 12/2004 | Eisermann et al. |
| 6,835,206 B2 | 12/2004 | Jackson |
| 6,837,905 B1 | 1/2005 | Lieberman |
| 6,863,688 B2 | 3/2005 | Ralph et al. |
| 6,863,689 B2 | 3/2005 | Ralph et al. |
| 6,875,213 B2 | 4/2005 | Michelson |
| 6,884,242 B2 | 4/2005 | LeHuec et al. |
| 6,896,676 B2 | 5/2005 | Zubok et al. |
| 6,908,484 B2 | 6/2005 | Zubok et al. |
| 6,918,934 B2 | 7/2005 | Ralph et al. |
| 6,923,814 B1 | 8/2005 | Hildebrand et al. |
| 6,936,071 B1 | 8/2005 | Marnay et al. |
| 6,972,021 B2 | 12/2005 | Raugel |
| 6,972,037 B2 | 12/2005 | Zubok et al. |
| 6,972,038 B2 | 12/2005 | Zubok et al. |
| 6,981,990 B2 | 1/2006 | Keller |
| 6,986,789 B2 | 1/2006 | Schultz et al. |
| 6,991,654 B2 | 1/2006 | Foley |
| 6,994,727 B2 | 2/2006 | Khandkar et al. |
| 6,994,728 B2 | 2/2006 | Zubok et al. |
| 6,994,729 B2 | 2/2006 | Zubok et al. |
| 6,997,954 B2 | 2/2006 | Zubok et al. |
| 6,997,955 B2 | 2/2006 | Zubok et al. |
| 7,022,139 B2 | 4/2006 | Errico et al. |
| 7,056,344 B2 | 6/2006 | Huppert et al. |
| 7,063,725 B2 | 6/2006 | Foley |
| 7,115,132 B2 | 10/2006 | Errico et al. |
| 7,118,579 B2 | 10/2006 | Michelson |
| 7,125,425 B2 | 10/2006 | Foley et al. |
| 7,147,642 B2 | 12/2006 | Grinberg et al. |
| 7,153,303 B2 | 12/2006 | Squires et al. |
| 7,153,304 B2 | 12/2006 | Robie et al. |
| 7,198,643 B2 | 4/2007 | Zubok et al. |
| 7,204,852 B2 | 4/2007 | Marnay et al. |
| 7,226,452 B2 | 6/2007 | Zubok et al. |
| 7,235,104 B2 | 6/2007 | Grinberg et al. |
| 7,238,203 B2 | 7/2007 | Bagga et al. |
| 7,270,679 B2 | 9/2007 | Istephanous et al. |
| 7,300,441 B2 | 11/2007 | Haid et al. |
| 7,320,689 B2 | 1/2008 | Keller |
| 7,537,614 B2 | 5/2009 | Baumgartner et al. |
| 7,794,465 B2 * | 9/2010 | Marik et al. ............ 606/87 |
| 2001/0005796 A1 | 6/2001 | Zdeblick et al. |
| 2001/0007073 A1 | 7/2001 | Zucherman et al. |
| 2001/0010001 A1 | 7/2001 | Michelson |
| 2001/0012938 A1 | 8/2001 | Zucherman et al. |
| 2001/0016773 A1 | 8/2001 | Serhan et al. |
| 2001/0016774 A1 | 8/2001 | Bresina et al. |
| 2001/0020170 A1 | 9/2001 | Zucherman et al. |
| 2001/0027343 A1 | 10/2001 | Keller |
| 2001/0039452 A1 | 11/2001 | Zucherman et al. |
| 2002/0004683 A1 | 1/2002 | Michelson |
| 2002/0017789 A1 | 2/2002 | Holmes et al. |
| 2002/0035400 A1 | 3/2002 | Bryan et al. |
| 2002/0045901 A1 | 4/2002 | Wagner et al. |
| 2002/0045904 A1 | 4/2002 | Fuss et al. |
| 2002/0062131 A1 | 5/2002 | Gallo |
| 2002/0082597 A1 | 6/2002 | Fraser |
| 2002/0082695 A1 | 6/2002 | Neumann |
| 2002/0082701 A1 | 6/2002 | Zdeblick et al. |
| 2002/0099377 A1 | 7/2002 | Zucherman et al. |
| 2002/0107571 A1 | 8/2002 | Foley |
| 2002/0107572 A1 | 8/2002 | Foley et al. |
| 2002/0111679 A1 | 8/2002 | Zucherman et al. |
| 2002/0111681 A1 | 8/2002 | Ralph et al. |
| 2002/0111682 A1 | 8/2002 | Ralph et al. |
| 2002/0111683 A1 | 8/2002 | Ralph et al. |
| 2002/0111684 A1 | 8/2002 | Ralph et al. |
| 2002/0111685 A1 | 8/2002 | Ralph et al. |
| 2002/0111686 A1 | 8/2002 | Ralph et al. |
| 2002/0111687 A1 | 8/2002 | Ralph et al. |
| 2002/0116009 A1 | 8/2002 | Fraser et al. |
| 2002/0123750 A1 | 9/2002 | Eisermann et al. |
| 2002/0128714 A1 | 9/2002 | Manasas et al. |
| 2002/0128715 A1 | 9/2002 | Bryan et al. |
| 2002/0143399 A1 | 10/2002 | Sutcliffe |
| 2002/0147450 A1 | 10/2002 | LeHuec et al. |
| 2002/0161375 A1 | 10/2002 | Ralph et al. |
| 2002/0169508 A1 | 11/2002 | Songer et al. |
| 2002/0177897 A1 | 11/2002 | Michelson |
| 2002/0188295 A1 | 12/2002 | Martz et al. |
| 2002/0193880 A1 | 12/2002 | Fraser |
| 2003/0009223 A1 | 1/2003 | Fehling et al. |
| 2003/0009224 A1 | 1/2003 | Kuras |
| 2003/0014057 A1 | 1/2003 | Ralph et al. |
| 2003/0014109 A1 | 1/2003 | Ralph et al. |
| 2003/0014110 A1 | 1/2003 | Ralph et al. |
| 2003/0014111 A1 | 1/2003 | Ralph et al. |
| 2003/0014112 A1 | 1/2003 | Ralph et al. |
| 2003/0014113 A1 | 1/2003 | Ralph et al. |
| 2003/0014114 A1 | 1/2003 | Ralph et al. |
| 2003/0014115 A1 | 1/2003 | Ralph et al. |
| 2003/0014116 A1 | 1/2003 | Ralph et al. |
| 2003/0023245 A1 | 1/2003 | Ralph et al. |
| 2003/0023309 A1 | 1/2003 | Ralph et al. |
| 2003/0023310 A1 | 1/2003 | Ralph et al. |
| 2003/0028197 A1 | 2/2003 | Hanson et al. |
| 2003/0028249 A1 | 2/2003 | Baccelli et al. |
| 2003/0028252 A1 | 2/2003 | Ralph et al. |
| 2003/0040796 A1 | 2/2003 | Ferree |
| 2003/0040801 A1 | 2/2003 | Ralph et al. |

| | | | | | | |
|---|---|---|---|---|---|---|
| 2003/0045939 A1 | 3/2003 | Casutt | | 2004/0068320 A1 | 4/2004 | Robie et al. |
| 2003/0055503 A1 | 3/2003 | O'Neil | | 2004/0073311 A1 | 4/2004 | Ferree |
| 2003/0060886 A1 | 3/2003 | Van Hoeck et al. | | 2004/0078079 A1 | 4/2004 | Foley |
| 2003/0065395 A1 | 4/2003 | Ralph et al. | | 2004/0092932 A1 | 5/2004 | Aubin et al. |
| 2003/0069586 A1 | 4/2003 | Errico et al. | | 2004/0106927 A1 | 6/2004 | Ruffner et al. |
| 2003/0069642 A1 | 4/2003 | Ralph et al. | | 2004/0117022 A1 | 6/2004 | Marnay et al. |
| 2003/0074064 A1 | 4/2003 | Gerbec et al. | | 2004/0133281 A1 | 7/2004 | Khandkar et al. |
| 2003/0074067 A1 | 4/2003 | Errico et al. | | 2004/0138750 A1 | 7/2004 | Mitchell |
| 2003/0078662 A1 | 4/2003 | Ralph et al. | | 2004/0143270 A1 | 7/2004 | Zucherman et al. |
| 2003/0078663 A1 | 4/2003 | Ralph et al. | | 2004/0143332 A1 | 7/2004 | Krueger et al. |
| 2003/0078664 A1 | 4/2003 | Ralph et al. | | 2004/0148028 A1 | 7/2004 | Ferree et al. |
| 2003/0078665 A1 | 4/2003 | Ralph et al. | | 2004/0167628 A1 | 8/2004 | Foley |
| 2003/0078666 A1 | 4/2003 | Ralph et al. | | 2004/0176772 A1 | 9/2004 | Zubok et al. |
| 2003/0078667 A1 | 4/2003 | Manasas et al. | | 2004/0176773 A1 | 9/2004 | Zubok et al. |
| 2003/0078668 A1 | 4/2003 | Michelson | | 2004/0176774 A1 | 9/2004 | Zubok et al. |
| 2003/0083747 A1 | 5/2003 | Winterbottom et al. | | 2004/0176777 A1 | 9/2004 | Zubok et al. |
| 2003/0083749 A1 | 5/2003 | Kuslich et al. | | 2004/0176778 A1 | 9/2004 | Zubok et al. |
| 2003/0093153 A1 | 5/2003 | Banick et al. | | 2004/0176843 A1 | 9/2004 | Zubok et al. |
| 2003/0100949 A1 | 5/2003 | Michelson | | 2004/0176852 A1 | 9/2004 | Zubok et al. |
| 2003/0100951 A1 | 5/2003 | Serhan et al. | | 2004/0193272 A1 | 9/2004 | Zubok et al. |
| 2003/0109928 A1 | 6/2003 | Pasquet et al. | | 2004/0215198 A1 | 10/2004 | Marnay et al. |
| 2003/0120344 A1 | 6/2003 | Michelson | | 2004/0220567 A1 | 11/2004 | Eisermann et al. |
| 2003/0125748 A1 | 7/2003 | Li et al. | | 2004/0220582 A1 | 11/2004 | Keller |
| 2003/0135213 A1 | 7/2003 | LeHuec et al. | | 2004/0233148 A1 | 11/2004 | Tanghe et al. |
| 2003/0135278 A1 | 7/2003 | Eckman | | 2004/0243240 A1 | 12/2004 | Beaurain et al. |
| 2003/0135279 A1 | 7/2003 | Michelson | | 2004/0267369 A1 | 12/2004 | Lyons et al. |
| 2003/0149438 A1 | 8/2003 | Nichols et al. | | 2005/0021042 A1 | 1/2005 | Marnay et al. |
| 2003/0149482 A1 | 8/2003 | Michelson | | 2005/0033430 A1 | 2/2005 | Powers et al. |
| 2003/0167091 A1 | 9/2003 | Scharf | | 2005/0043800 A1 | 2/2005 | Paul et al. |
| 2003/0167092 A1 | 9/2003 | Foley | | 2005/0043803 A1 | 2/2005 | Schultz et al. |
| 2003/0171813 A1 | 9/2003 | Kiester | | 2005/0055029 A1 | 3/2005 | Marik et al. |
| 2003/0176921 A1 | 9/2003 | Lawson | | 2005/0071013 A1 | 3/2005 | Zubok et al. |
| 2003/0176922 A1 | 9/2003 | Lawson et al. | | 2005/0072822 A1 | 4/2005 | Stotts |
| 2003/0176923 A1 | 9/2003 | Keller et al. | | 2005/0085917 A1 | 4/2005 | Marnay et al. |
| 2003/0181982 A1 | 9/2003 | Kuslich | | 2005/0113842 A1 | 5/2005 | Bertagnoli et al. |
| 2003/0187453 A1 | 10/2003 | Schlapfer et al. | | 2005/0119665 A1 | 6/2005 | Keller |
| 2003/0187454 A1 | 10/2003 | Gill et al. | | 2005/0143749 A1 | 6/2005 | Zalenski et al. |
| 2003/0187508 A1 | 10/2003 | Cauthen | | 2005/0159819 A1 | 7/2005 | McCormack et al. |
| 2003/0191534 A1 | 10/2003 | Viart et al. | | 2005/0165406 A1 | 7/2005 | Assell et al. |
| 2003/0195632 A1 | 10/2003 | Foley et al. | | 2005/0165487 A1 | 7/2005 | Muhanna et al. |
| 2003/0199981 A1 | 10/2003 | Ferree | | 2005/0197705 A1 | 9/2005 | Arnin et al. |
| 2003/0199983 A1 | 10/2003 | Michelson | | 2005/0203533 A1 | 9/2005 | Ferguson et al. |
| 2003/0204260 A1 | 10/2003 | Ferree | | 2005/0228497 A1 | 10/2005 | Ferree et al. |
| 2003/0208271 A1 | 11/2003 | Kuras | | 2005/0228500 A1 | 10/2005 | Kim et al. |
| 2003/0208273 A1 | 11/2003 | Eisermann et al. | | 2005/0240270 A1 | 10/2005 | Zubok et al. |
| 2003/0208274 A1 | 11/2003 | Davis | | 2005/0240271 A1 | 10/2005 | Zubok et al. |
| 2003/0216744 A1 | 11/2003 | Longhini et al. | | 2005/0240272 A1 | 10/2005 | Zubok et al. |
| 2003/0216810 A1 | 11/2003 | Ralph et al. | | 2005/0240273 A1 | 10/2005 | Khandkar et al. |
| 2003/0220690 A1 | 11/2003 | Cauthen | | 2005/0256577 A1 | 11/2005 | Baumgartner et al. |
| 2003/0220694 A1 | 11/2003 | Cauthen | | 2005/0267581 A1 | 12/2005 | Marnay et al. |
| 2003/0225408 A1 | 12/2003 | Nichols et al. | | 2005/0267582 A1 | 12/2005 | Ferree et al. |
| 2003/0225416 A1 | 12/2003 | Bonvallet et al. | | 2005/0283237 A1 | 12/2005 | Zucherman et al. |
| 2003/0229358 A1 | 12/2003 | Errico et al. | | 2006/0004377 A1 | 1/2006 | Keller |
| 2003/0229397 A1 | 12/2003 | Davis | | 2006/0030857 A1 | 2/2006 | de Villiers et al. |
| 2003/0233097 A1 | 12/2003 | Ferree | | 2006/0036326 A1 | 2/2006 | Baumgartner et al. |
| 2003/0233145 A1 | 12/2003 | Landry et al. | | 2006/0064100 A1 | 3/2006 | Bertagnoli et al. |
| 2003/0233148 A1 | 12/2003 | Ferree | | 2006/0069439 A1 | 3/2006 | Zucherman et al. |
| 2003/0236520 A1 | 12/2003 | Lim et al. | | 2006/0085077 A1 | 4/2006 | Cook et al. |
| 2004/0002758 A1 | 1/2004 | Landry et al. | | 2006/0100634 A1 | 5/2006 | Ferguson |
| 2004/0002759 A1 | 1/2004 | Ferree | | 2006/0116768 A1 | 6/2006 | Krueger et al. |
| 2004/0002761 A1 | 1/2004 | Rogers et al. | | 2006/0129160 A1 | 6/2006 | Liu et al. |
| 2004/0002762 A1 | 1/2004 | Hawkins | | 2006/0149273 A1 | 7/2006 | Ross et al. |
| 2004/0006343 A1 | 1/2004 | Sevrain | | 2006/0149278 A1 | 7/2006 | Abdou |
| 2004/0010254 A1 | 1/2004 | Cook et al. | | 2006/0167461 A1 | 7/2006 | Hawkins et al. |
| 2004/0010316 A1 | 1/2004 | William et al. | | 2006/0178748 A1 | 8/2006 | Dinger et al. |
| 2004/0021042 A1 | 2/2004 | Stephen et al. | | 2006/0195114 A1 | 8/2006 | Bertagnoli |
| 2004/0022582 A1 | 2/2004 | Sick | | 2006/0200166 A1 | 9/2006 | Hanson et al. |
| 2004/0024406 A1 | 2/2004 | Ralph et al. | | 2006/0217731 A1 | 9/2006 | Gil et al. |
| 2004/0024407 A1 | 2/2004 | Ralph et al. | | 2006/0235422 A1 | 10/2006 | Keller |
| 2004/0024459 A1 | 2/2004 | Ferree | | 2006/0247645 A1 | 11/2006 | Wilcox et al. |
| 2004/0024461 A1 | 2/2004 | Ferree | | 2006/0247649 A1 | 11/2006 | Rezach et al. |
| 2004/0024462 A1 | 2/2004 | Ferree et al. | | 2006/0282020 A1 | 12/2006 | Bertagnoli et al. |
| 2004/0030387 A1 | 2/2004 | Landry et al. | | 2007/0073403 A1 | 3/2007 | Lombardo et al. |
| 2004/0030389 A1 | 2/2004 | Ferree | | 2007/0073405 A1 | 3/2007 | Verhulst et al. |
| 2004/0030390 A1 | 2/2004 | Ferree | | 2007/0106388 A1 | 5/2007 | Michelson |
| 2004/0030391 A1 | 2/2004 | Ferree | | 2007/0112429 A1 | 5/2007 | Muhanna et al. |
| 2004/0034426 A1 | 2/2004 | Errico et al. | | 2007/0118145 A1 | 5/2007 | Fischer et al. |
| 2004/0039387 A1* | 2/2004 | Gause et al. ............ 606/69 | | 2007/0118224 A1 | 5/2007 | Shah et al. |
| 2004/0068318 A1 | 4/2004 | Coates et al. | | 2007/0123989 A1 | 5/2007 | Gfeller et al. |

| | | | |
|---|---|---|---|
| 2007/0191856 A1 | 8/2007 | Gil et al. | |
| 2007/0213820 A1 | 9/2007 | Magerl et al. | |
| 2007/0225813 A1 | 9/2007 | Haines | |
| 2007/0265707 A1 | 11/2007 | Marnay et al. | |
| 2007/0282448 A1 | 12/2007 | Abdou | |
| 2008/0027548 A9 | 1/2008 | Ferree et al. | |
| 2008/0033563 A1 | 2/2008 | Khandkar et al. | |
| 2008/0077155 A1 | 3/2008 | Diederich et al. | |
| 2008/0082169 A1 | 4/2008 | Gittings et al. | |
| 2009/0018663 A1 | 1/2009 | Cook et al. | |

FOREIGN PATENT DOCUMENTS

| | | |
|---|---|---|
| DE | 43 15 757 | 11/1994 |
| DE | 199 03 763 A1 | 8/2000 |
| DE | 10130825 A1 | 3/2002 |
| EP | 0 392 076 A1 | 10/1990 |
| EP | 0 599 419 A2 | 6/1994 |
| EP | 599419 A2 | 6/1994 |
| EP | 1 222 903 A1 | 7/2002 |
| EP | 1219266 A1 | 7/2002 |
| FR | 2 718 635 A1 | 10/1995 |
| FR | 2 730159 A1 | 8/1996 |
| FR | 2 805 985 A1 | 9/2001 |
| FR | 2 824 261 A1 | 11/2002 |
| RU | 2 077 288 C1 | 4/1997 |
| SU | 1560184 | 4/1990 |
| WO | 91/13598 A1 | 9/1991 |
| WO | 94/04100 A1 | 3/1994 |
| WO | 9509587 A1 | 4/1995 |
| WO | 97/10776 A2 | 3/1997 |
| WO | 9710780 A1 | 3/1997 |
| WO | 0024342 A1 | 5/2000 |
| WO | 0101893 A1 | 1/2001 |
| WO | 01/62191 A2 | 8/2001 |
| WO | 01/93785 | 12/2001 |
| WO | 01/93786 A2 | 12/2001 |
| WO | 03/084449 A1 | 10/2003 |
| WO | 03090649 A1 | 11/2003 |
| WO | 2004/019828 A1 | 3/2004 |
| WO | 2004/026186 A1 | 4/2004 |

* cited by examiner

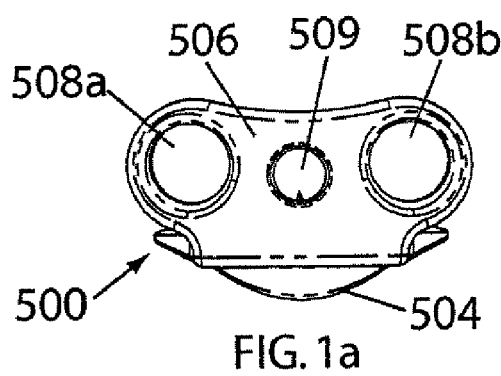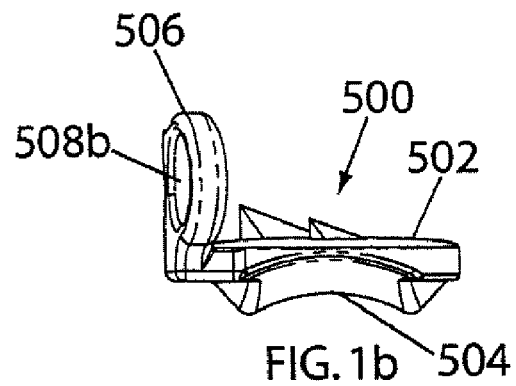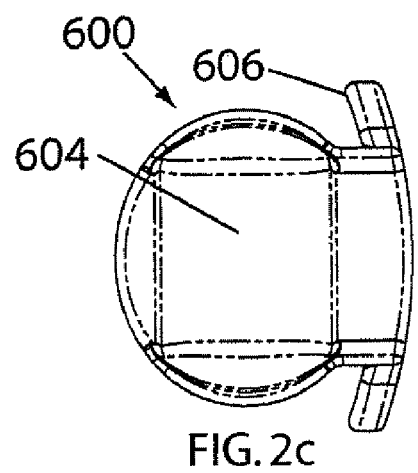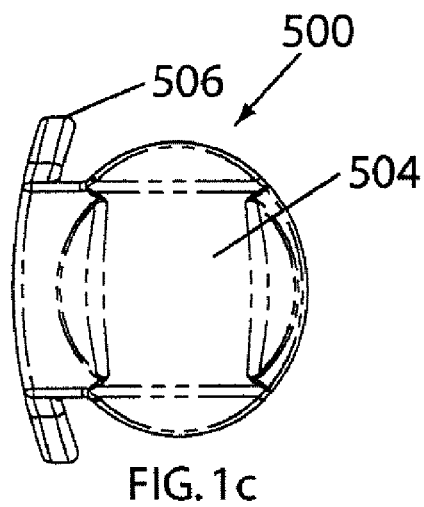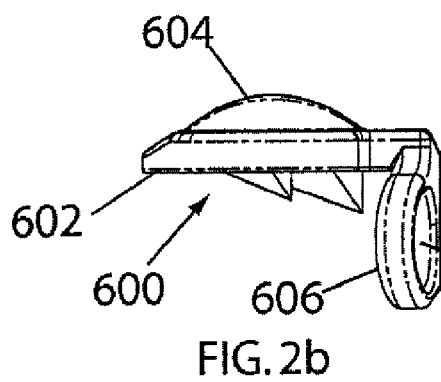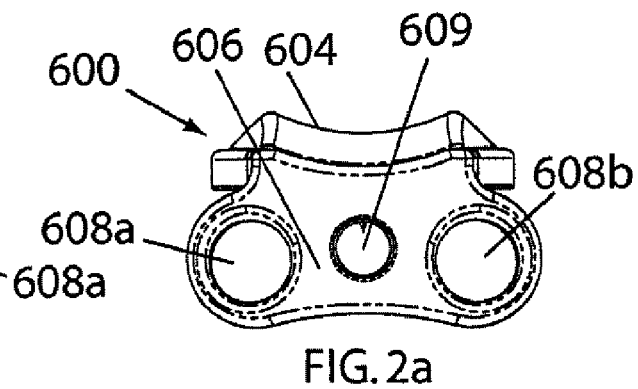

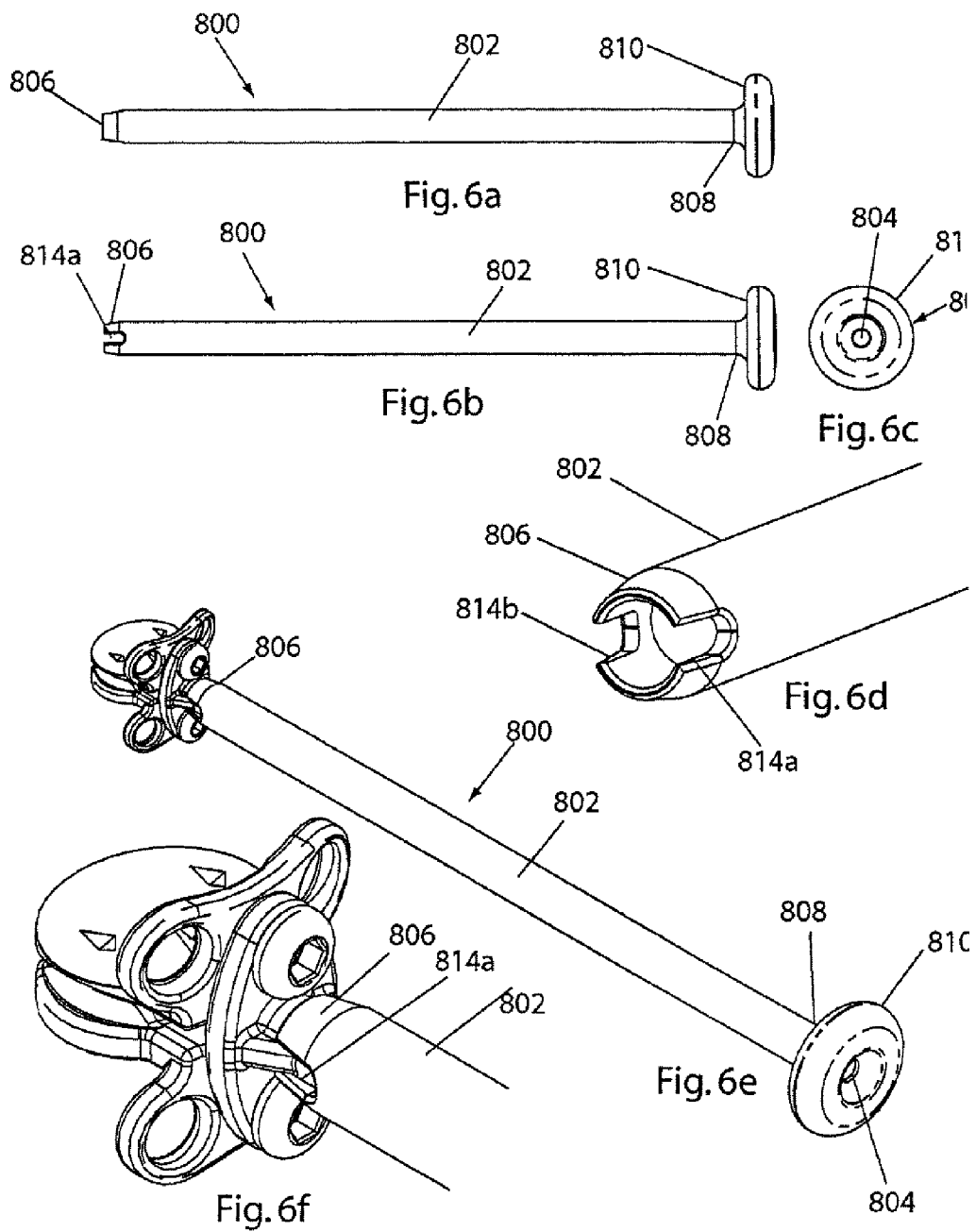

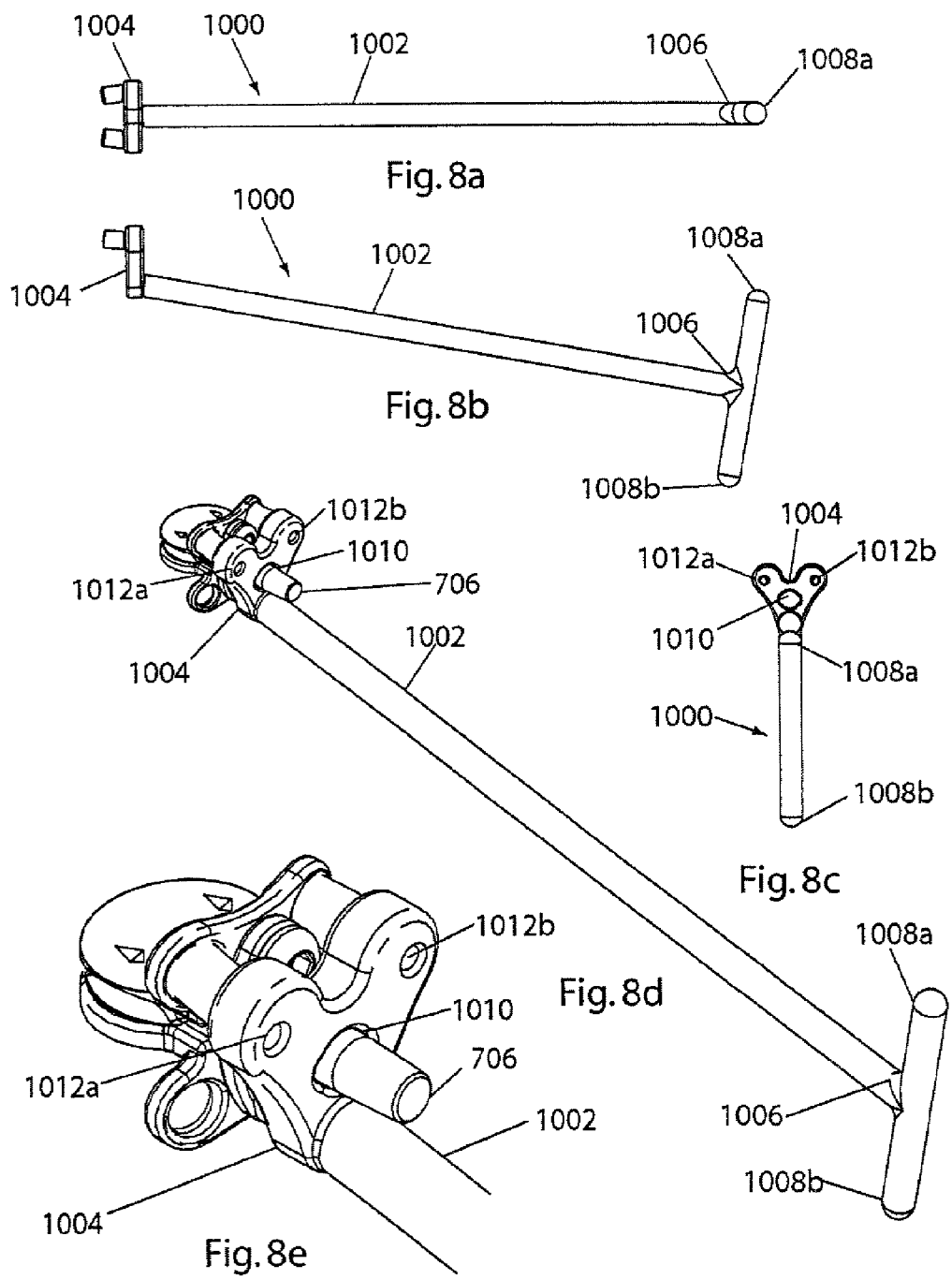

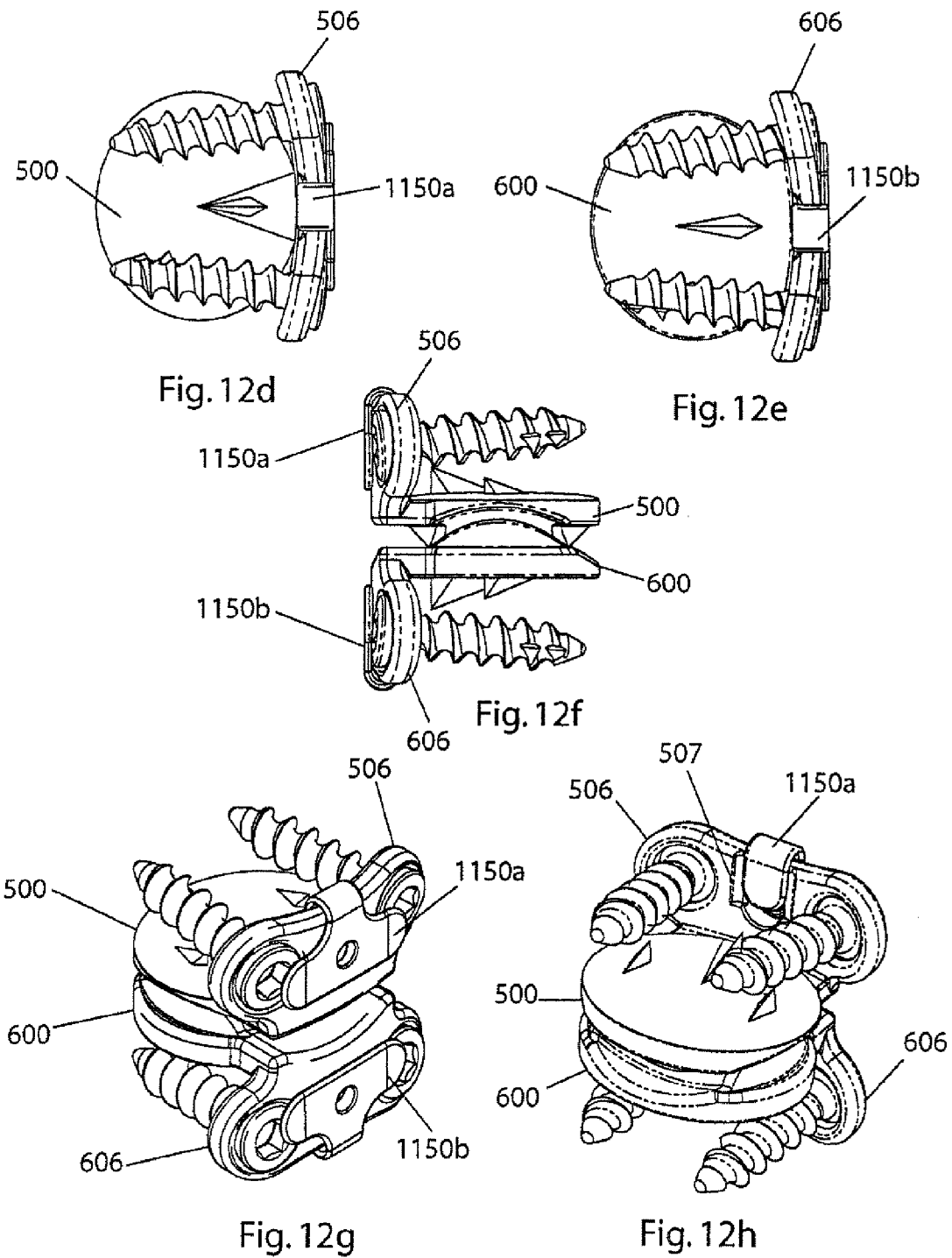

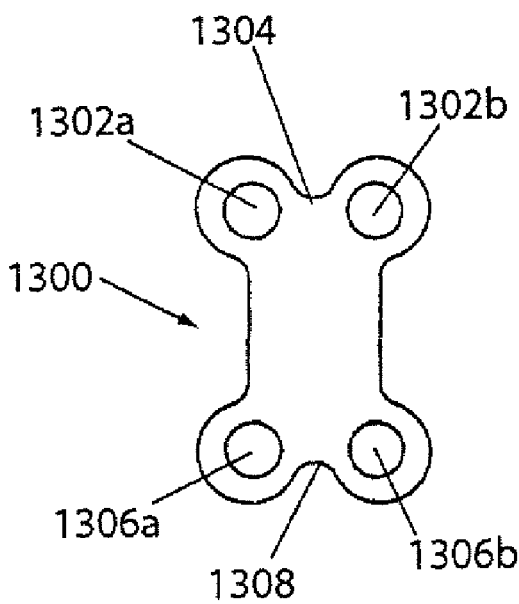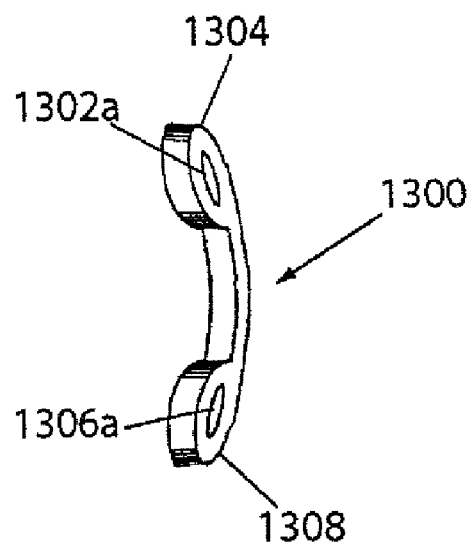
Fig. 13a  Fig. 13b
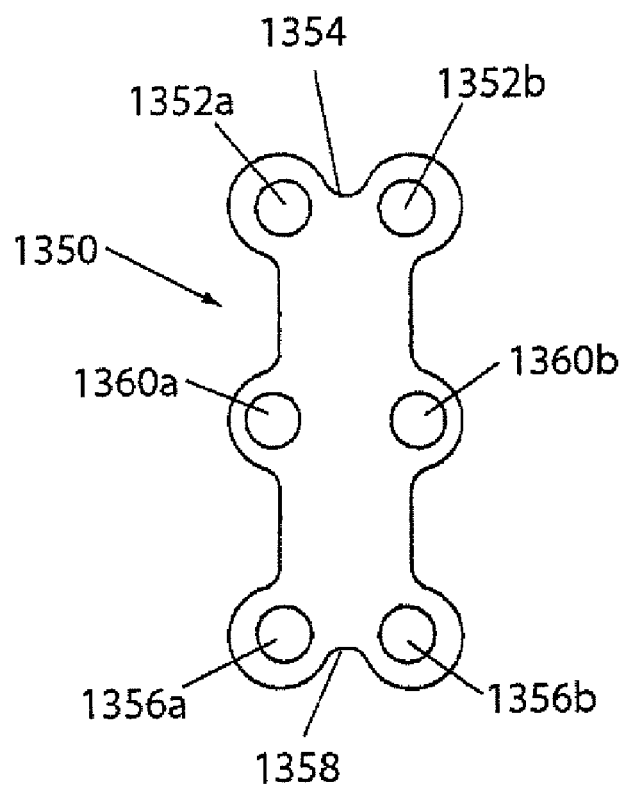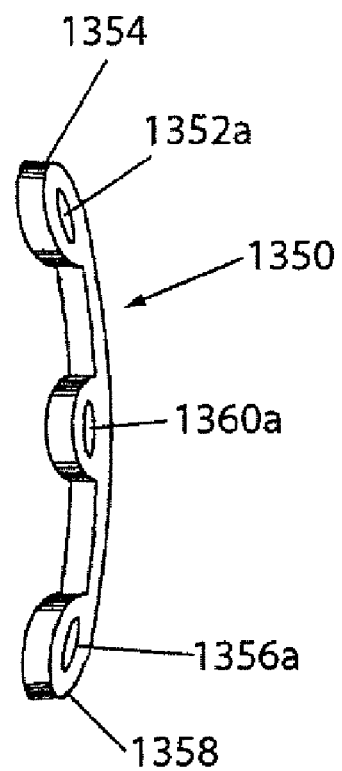
Fig. 13c  Fig. 13d

INSTRUMENTATION AND METHODS FOR USE IN IMPLANTING A CERVICAL DISC REPLACEMENT DEVICE

CROSS-REFERENCE TO RELATED APPLICATIONS

This application is a divisional of U.S. patent application Ser. No. 10/781,505, (filed Feb. 18, 2004) entitled "Instrumentation and Methods for Use in Implanting a Cervical Disc Replacement Device" which is a continuation of U.S. patent application Ser. No. 10/688,632 (filed Oct. 17, 2003) entitled "Instrumentation and Methods for Use in Implanting a Cervical Disc Replacement Device", which is a continuation in part of U.S. patent application Ser. No. 10/382,702 (filed Mar. 6, 2003) entitled "Cervical Disc Replacement", the disclosures of which are hereby incorporated by reference herein in their entireties.

FIELD OF THE INVENTION

This invention relates generally to systems and methods for use in spine arthroplasty, and more specifically to instruments for inserting and removing cervical disc replacement trials, and inserting and securing cervical disc replacement devices, and methods of use thereof.

BACKGROUND OF THE INVENTION

The structure of the intervertebral disc disposed between the cervical bones in the human spine comprises a peripheral fibrous shroud (the annulus) which circumscribes a spheroid of flexibly deformable material (the nucleus). The nucleus comprises a hydrophilic, elastomeric cartilaginous substance that cushions and supports the separation between the bones while also permitting articulation of the two vertebral bones relative to one another to the extent such articulation is allowed by the other soft tissue and bony structures surrounding the disc. The additional bony structures that define pathways of motion in various modes include the posterior joints (the facets) and the lateral intervertebral joints (the uncovertebral joints). Soft tissue components, such as ligaments and tendons, constrain the overall segmental motion as well.

Traumatic, genetic, and long term wearing phenomena contribute to the degeneration of the nucleus in the human spine. This degeneration of this critical disc material, from the hydrated, elastomeric material that supports the separation and flexibility of the vertebral bones, to a flattened and inflexible state, has profound effects on the mobility (instability and limited ranges of appropriate motion) of the segment, and can cause significant pain to the individual suffering from the condition. Although the specific causes of pain in patients suffering from degenerative disc disease of the cervical spine have not been definitively established, it has been recognized that pain may be the result of neurological implications (nerve fibers being compressed) and/or the subsequent degeneration of the surrounding tissues (the arthritic degeneration of the facet joints) as a result of their being overloaded.

Traditionally, the treatment of choice for physicians caring for patients who suffer from significant degeneration of the cervical intervertebral disc is to remove some, or all, of the damaged disc. In instances in which a sufficient portion of the intervertebral disc material is removed, or in which much of the necessary spacing between the vertebrae has been lost (significant subsidence), restoration of the intervertebral separation is required.

Unfortunately, until the advent of spine arthroplasty devices, the only methods known to surgeons to maintain the necessary disc height necessitated the immobilization of the segment. Immobilization is generally achieved by attaching metal plates to the anterior or posterior elements of the cervical spine, and the insertion of some osteoconductive material (autograft, allograft, or other porous material) between the adjacent vertebrae of the segment. This immobilization and insertion of osteoconductive material has been utilized in pursuit of a fusion of the bones, which is a procedure carried out on tens of thousands of pain suffering patients per year.

This sacrifice of mobility at the immobilized, or fused, segment, however, is not without consequences. It was traditionally held that the patient's surrounding joint segments would accommodate any additional articulation demanded of them during normal motion by virtue of the fused segment's immobility. While this is true over the short-term (provided only one, or at most two, segments have been fused), the effects of this increased range of articulation demanded of these adjacent segments has recently become a concern. Specifically, an increase in the frequency of returning patients who suffer from degeneration at adjacent levels has been reported.

Whether this increase in adjacent level deterioration is truly associated with rigid fusion, or if it is simply a matter of the individual patient's predisposition to degeneration is unknown. Either way, however, it is clear that a progressive fusion of a long sequence of vertebrae is undesirable from the perspective of the patient's quality of life as well as from the perspective of pushing a patient to undergo multiple operative procedures.

While spine arthroplasty has been developing in theory over the past several decades, and has even seen a number of early attempts in the lumbar spine show promising results, it is only recently that arthoplasty of the spine has become a truly realizable promise. The field of spine arthroplasty has several classes of devices. The most popular among these are: (a) the nucleus replacements, which are characterized by a flexible container filled with an elastomeric material that can mimic the healthy nucleus; and (b) the total disc replacements, which are designed with rigid endplates which house a mechanical articulating structure that attempts to mimic and promote the healthy segmental motion.

Among these solutions, the total disc replacements have begun to be regarded as the most probable long-term treatments for patients having moderate to severe lumbar disc degeneration. In the cervical spine, it is likely that these mechanical solutions will also become the treatment of choice.

It is an object of the invention to provide instrumentation and methods that enable surgeons to more accurately, easily, and efficiently implant fusion or non-fusion cervical disc replacement devices. Other objects of the invention not explicitly stated will be set forth and will be more clearly understood in conjunction with the descriptions of the preferred embodiments disclosed hereafter.

SUMMARY OF THE INVENTION

The preceding objects are achieved by the invention, which includes cervical disc replacement trials, cervical disc replacement devices, cervical disc replacement device insertion instrumentation (including, e.g., an insertion plate with mounting screws, an insertion handle, and an insertion pusher), and cervical disc replacement device fixation instrumentation (including, e.g., drill guides, drill bits, screwdrivers, bone screws, and retaining clips).

More particularly, the devices, instrumentation, and methods disclosed herein are intended for use in spine arthroplasty procedures, and specifically for use with the devices, instrumentation, and methods described herein in conjunction with the devices, instrumentation, and methods described herein and in the '702 application. However, it should be understood that the devices, instrumentation, and methods described herein are also suitable for use with other intervertebral disc replacement devices, instrumentation, and methods without departing from the scope of the invention.

For example, while the trials described herein are primarily intended for use in distracting an intervertebral space and/or determining the appropriate size of cervical disc replacement devices (e.g., described herein and in the '702 application) to be implanted (or whether a particular size can be implanted) into the distracted intervertebral space, they can also be used for determining the appropriate size of any other suitably configured orthopedic implant or trial to be implanted (or whether a particular size can be implanted) into the distracted intervertebral space. And, for example, while the insertion instrumentation described herein is primarily intended for use in holding, inserting, and otherwise manipulating cervical disc replacement devices (e.g., described herein and, in suitably configured embodiments, in the '702 application), it can also be used for manipulating any other suitably configured orthopedic implant or trial. And, for example, while the fixation instrumentation described herein is primarily intended for use in securing within the intervertebral space the cervical disc replacement devices (e.g., described herein and, in suitably configured embodiments, in the '702 application), it can also be used with any other suitably configured orthopedic implant or trial.

While the instrumentation described herein (e.g., the trials, insertion instrumentation, and fixation instrumentation) will be discussed for use with the cervical disc replacement device of FIGS. 1a-3f herein, such discussions are merely by way of example and not intended to be limiting of their uses. Thus, it should be understood that the tools can be used with suitably configured embodiments of the cervical disc replacement devices disclosed in the '702 application, or any other artificial intervertebral disc having (or being modifiable or modified to have) suitable features therefor. Moreover, it is anticipated that the features of the cervical disc replacement device (e.g., the flanges, bone screw holes, and mounting holes) that are used by the tools discussed herein to hold and/or manipulate these devices (some of such features, it should be noted, were first shown and disclosed in the '702 application) can be applied, individually or collectively or in various combinations, to other trials, spacers, artificial intervertebral discs, or other orthopedic devices as stand-alone innovative features for enabling such trials, spacers, artificial intervertebral discs, or other orthopedic devices to be more efficiently and more effectively held and/or manipulated by the tools described herein or by other tools having suitable features. In addition, it should be understood that the invention encompasses artificial intervertebral discs, spacers, trials, and/or other orthopedic devices, that have one or more of the features disclosed herein, in any combination, and that the invention is therefore not limited to artificial intervertebral discs, spacers, trials, and/or other orthopedic devices having all of the features simultaneously.

The cervical disc replacement device of FIGS. 1a-3f is an alternate embodiment of the cervical disc replacement device of the '702 application. The illustrated alternate embodiment of the cervical disc replacement device is identical in structure to the cervical disc replacement device in the '702 application, with the exception that the vertebral bone attachment flanges are configured differently, such that they are suitable for engagement by the instrumentation described herein.

More particularly, in this alternate embodiment, the flange of the upper element extends upwardly from the anterior edge of the upper element, and has a lateral curvature that approximates the curvature of the anterior periphery of the upper vertebral body against which it is to be secured. The attachment flange is provided with a flat recess, centered on the midline, that accommodates a clip of the present invention. The attachment flange is further provided with two bone screw holes symmetrically disposed on either side of the midline. The holes have longitudinal axes directed along preferred bone screw driving lines. Centrally between the bone screw holes, a mounting screw hole is provided for attaching the upper element to an insertion plate of the present invention for implantation. The lower element is similarly configured with a similar oppositely extending flange.

Once the surgeon has prepared the intervertebral space, the surgeon may use one or more cervical disc replacement trials of the present invention to distract the intervertebral space and determine the appropriate size of a cervical disc replacement device to be implanted (or whether a particular size of the cervical disc replacement device can be implanted) into the distracted cervical intervertebral space. Preferably, for each cervical disc replacement device to be implanted, a plurality of sizes of the cervical disc replacement device would be available. Accordingly, preferably, each of the plurality of trials for use with a particular plurality of differently sized cervical disc replacement devices would have a respective oval footprint and depth dimension set corresponding to the footprint and depth dimension set of a respective one of the plurality of differently sized cervical disc replacement devices.

Each of the cervical disc replacement trials includes a distal end configured to approximate relevant dimensions of an available cervical disc replacement device. The distal end has a head with an oval footprint. The upper surface of the head is convex, similar to the configuration of the vertebral body contact surface of the upper element of the cervical disc replacement device (but without the teeth). The lower surface of the head is flat, similar to the configuration of the vertebral body contact surface of the lower element of the cervical disc replacement device (but without the teeth). The cervical disc replacement trial, not having the teeth, can be inserted and removed from the intervertebral space without compromising the endplate surfaces. The cervical disc replacement trial further has a vertebral body stop disposed at the anterior edge of the head, to engage the anterior surface of the upper vertebral body before the trial is inserted too far into the intervertebral space.

Accordingly, the surgeon can insert and remove at least one of the trials (or more, as necessary) from the prepared intervertebral space. As noted above, the trials are useful for distracting the prepared intervertebral space. For example, starting with the largest distractor that can be wedged in between the vertebral bones, the surgeon will insert the trial head and then lever the trial handle up and down to loosen the annulus and surrounding ligaments to urge the bone farther apart. The surgeon then removes the trial head from the intervertebral space, and replaces it with the next largest (in terms of height) trial head. The surgeon then levers the trial handle up and down to further loosen the annulus and ligaments. The surgeon then proceeds to remove and replace the trial head with the next largest (in terms of height) trial head, and continues in this manner with larger and larger trials until the intervertebral space is distracted to the appropriate height.

Regardless of the distraction method used, the cervical disc replacement trials are useful for finding the cervical disc replacement device size that is most appropriate for the prepared intervertebral space, because each of the trial heads approximates the relevant dimensions of an available cervical disc replacement device. Once the intervertebral space is distracted, the surgeon can insert and remove one or more of the trial heads to determine the appropriate size of cervical disc replacement device to use. Once the appropriate size is determined, the surgeon proceeds to implant the selected cervical disc replacement device.

An insertion plate of the present invention is mounted to the cervical disc replacement device to facilitate a preferred simultaneous implantation of the upper and lower elements of the replacement device. The upper and lower elements are held by the insertion plate in an aligned configuration preferable for implantation. A ledge on the plate maintains a separation between the anterior portions of the inwardly facing surfaces of the elements to help establish and maintain this preferred relationship. The flanges of the elements each have a mounting screw hole and the insertion plate has two corresponding mounting holes. Mounting screws are secured through the colinear mounting screw hole pairs, such that the elements are immovable with respect to the insertion plate and with respect to one another. In this configuration, the upper element, lower element, and insertion plate construct is manipulatable as a single unit.

An insertion handle of the present invention is provided primarily for engaging an anteriorly extending stem of the insertion plate so that the cervical disc replacement device and insertion plate construct can be manipulated into and within the treatment site. The insertion handle has a shaft with a longitudinal bore at a distal end and a flange at a proximal end. Longitudinally aligning the insertion handle shaft with the stem, and thereafter pushing the hollow distal end of the insertion handle shaft toward the insertion plate, causes the hollow distal end to friction-lock to the outer surface of the stem. Once the insertion handle is engaged with the insertion plate, manipulation of the insertion handle shaft effects manipulation of the cervical disc replacement device and insertion plate construct. The surgeon can therefore insert the construct into the treatment area. More particularly, after the surgeon properly prepares the intervertebral space, the surgeon inserts the cervical disc replacement device into the intervertebral space from an anterior approach, such that the upper and lower elements are inserted between the adjacent vertebral bones with the element footprints fitting within the perimeter of the intervertebral space and with the teeth of the elements' vertebral body contact surfaces engaging the vertebral endplates, and with the flanges of the upper and lower elements flush against the anterior faces of the upper and lower vertebral bones, respectively.

Once the construct is properly positioned in the treatment area, the surgeon uses an insertion pusher of the present invention to disengage the insertion handle shaft from the stem of the insertion plate. The insertion pusher has a longitudinal shaft with a blunt distal end and a proximal end with a flange. The shaft of the insertion pusher can be inserted into and translated within the longitudinal bore of the insertion handle shaft. Because the shaft of the insertion pusher is as long as the longitudinal bore of the insertion handle shaft, the flange of the insertion handle and the flange of the insertion pusher are separated by a distance when the pusher shaft is inserted all the way into the longitudinal bore until the blunt distal end of the shaft contacts the proximal face of the insertion plate stem. Accordingly, a bringing together of the flanges (e.g., by the surgeon squeezing the flanges toward one another) will overcome the friction lock between the distal end of the insertion handle shaft and the stem of the insertion plate.

Once the insertion handle has been removed, the surgeon uses a drill guide of the present invention to guide the surgeon's drilling of bone screws through the bone screw holes of the upper and lower elements' flanges and into the vertebral bones. The drill guide has a longitudinal shaft with a distal end configured with a central bore that accommodates the stem so that the drill guide can be placed on and aligned with the stem. The distal end is further configured to have two guide bores that have respective longitudinal axes at preferred bone screw drilling paths relative to one another. When the central bore is disposed on the stem of the insertion plate, the drill guide shaft can be rotated on the stem into either of two preferred positions in which the guide bores are aligned with the bone screw holes on one of the flanges, or with the bone screw holes on the other flange.

To secure the upper element flange to the upper vertebral body, the surgeon places the drill guide shaft onto the stem of the insertion plate, and rotates the drill guide into the first preferred position. Using a suitable bone drill and cooperating drill bit, the surgeon drills upper tap holes for the upper bone screws. The surgeon then rotates the drill guide shaft on the stem of the insertion plate until the guide bores no longer cover the upper bone screw holes. The surgeon can then screw the upper bone screws into the upper tap holes using a suitable surgical bone screw driver. To then secure the lower element flange to the lower vertebral body, the surgeon further rotates the drill guide shaft on the stem of the insertion plate until the drill guide is in the second preferred position, and proceeds to drill the lower bone screw tap holes and screw the lower bone screws into them in the same manner.

Once the upper and lower elements are secured to the adjacent vertebral bones, the surgeon removes the drill guide from the stem of the insertion plate and from the treatment area. Using a suitable surgical screw driver, the surgeon then removes the mounting screws that hold the insertion plate against the elements' flanges and removes the insertion plate and the mounting screws from the treatment area.

Once the mounting screws and the insertion plate are removed, the surgeon uses a clip applicator of the present invention to mount retaining clips on the flanges to assist in retaining the bone screws. Each of the clips has a central attachment bore and, extending therefrom, a pair of oppositely directed laterally extending flanges and an upwardly (or downwardly) extending hooked flange. The clips can be snapped onto the element flanges (one clip onto each flange). Each of the laterally extending flanges of the clip is sized to cover at least a portion of a respective one of the bone screw heads when the clip is attached in this manner to the flange so that the clips help prevent the bone screws from backing out.

Also disclosed is an alternate dual cervical disc replacement device configuration suitable, for example, for implantation into two adjacent cervical intervertebral spaces. The configuration includes an alternate, upper, cervical disc replacement device (including an upper element and an alternate lower element), for implantation into an upper cervical intervertebral space, and further includes an alternate, lower, cervical disc replacement device (including an alternate upper element and a lower element), for implantation into an adjacent, lower, cervical intervertebral space. The illustrated alternate, upper, embodiment is identical in structure to the cervical disc replacement device of FIGS. 1a-3f, with the exception that the flange of the lower element is configured differently and without bone screw holes. The illustrated alternate, lower, embodiment is identical in structure to the cervical disc replacement device of FIGS. 1a-3f, with the exception that the flange of the upper element is configured differently and without bone screw holes.

More particularly, in the alternate, upper, cervical disc replacement device of this alternate configuration, the flange of the alternate lower element does not have bone screw holes, but does have a mounting screw hole for attaching the alternate lower element to an alternate, upper, insertion plate. Similarly, in the alternate, lower, cervical disc replacement device of this alternate configuration, the flange of the alternate upper element does not have bone screw holes, but does have a mounting screw hole for attaching the alternate upper element to an alternate, lower, insertion plate. The extent of the flange of the alternate lower element is laterally offset to the right (in an anterior view) from the midline, and the extent of the flange of the alternate upper element is laterally offset to the left (in an anterior view) from the midline, so that the flanges avoid one another when the alternate lower element of the alternate, upper, cervical disc replacement device, and the alternate upper element of the alternate, lower, cervical disc replacement device, are implanted in this alternate configuration.

The alternate, upper, insertion plate is identical in structure to the insertion plate described above, with the exception that the lower flange is offset from the midline (to the right in an anterior view) to align its mounting screw hole with the offset mounting screw hole of the alternate lower element. Similarly, the alternate, lower, insertion plate is identical in structure to the insertion plate described above, with the exception that the upper flange is offset from the midline (to the left in an anterior view) to align its mounting screw hole with the offset mounting screw hole of the alternate upper element.

Accordingly, the upper and lower elements of the alternate, upper, cervical disc replacement device, being held by the alternate upper insertion plate, as well as the upper and lower elements of the alternate, lower, cervical disc replacement device, being held by the alternate lower insertion plate, can be implanted using the insertion handle, insertion pusher, drill guide, clips (one on the uppermost element flange, and one on the lowermost element flange, because only the uppermost element and the lowermost element are secured by bone screws), and clip applicator, in the manner described above with respect to the implantation of the cervical disc replacement device.

BRIEF DESCRIPTION OF THE DRAWINGS

FIGS. 1a-c show anterior (FIG. 1a), lateral (FIG. 1b), and bottom (FIG. 1c) views of a top element of a cervical disc replacement device of the invention.

FIGS. 2a-c show anterior (FIG. 2a), lateral (FIG. 2b), and top (FIG. 2c) views of a bottom element of the cervical disc replacement device.

FIGS. 6a-d show top (FIG. 6a), lateral (FIG. 6b), anterior (FIG. 6c), and postero-lateral (FIG. 6d) views of an insertion handle of the insertion instrumentation of the present invention. FIG. 6e shows an antero-lateral perspective view of the insertion handle attached to the insertion plate. FIG. 6f shows a magnified view of the distal end of FIG. 6e.

FIGS. 8a-c show top (FIG. 8a), lateral (FIG. 8b), and anterior (FIG. 8c) views of a drill guide of the insertion instrumentation of the present invention. FIG. 8d shows an antero-lateral perspective view of the drill guide inserted onto the insertion plate. FIG. 8e shows a magnified view of the distal end of FIG. 8d.

FIGS. 12b-h show anterior (FIG. 12b), posterior (FIG. 12c), top (FIG. 12d), bottom (FIG. 12e), lateral (FIG. 12f), antero-lateral perspective (FIG. 12g), and postero-lateral perspective (FIG. 12h) views of the cervical disc replacement device after the retaining clips have been applied.

FIGS. 13a-b show a prior art one level cervical fusion plate in anterior (FIG. 13a) and lateral (FIG. 13b) views. FIGS. 13c-d show a prior art two level cervical fusion plate in anterior (FIG. 13c) and lateral (FIG. 13d) views.

DETAILED DESCRIPTION OF THE PREFERRED EMBODIMENTS

Figure 3A:
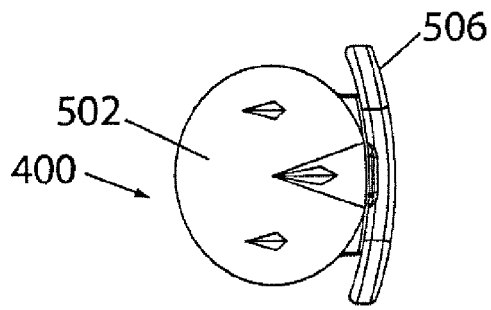
FIGS. 3a-f show top (FIG. 3a), lateral (FIG. 3b), anterior (FIG. 3c), posterior (FIG. 3d), antero-lateral perspective (FIG. 3e), and postero-lateral perspective (FIG. 3f) views of the cervical disc replacement device, assembled with the top and bottom elements of FIGS. 1a-c and 2a-c.
Figure 3B:
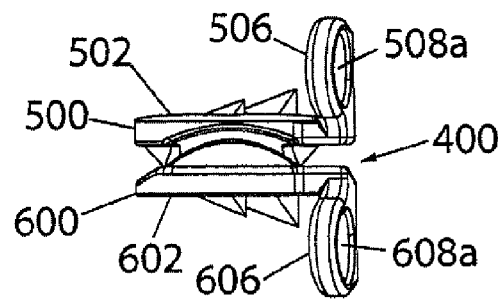
Figure 3C:
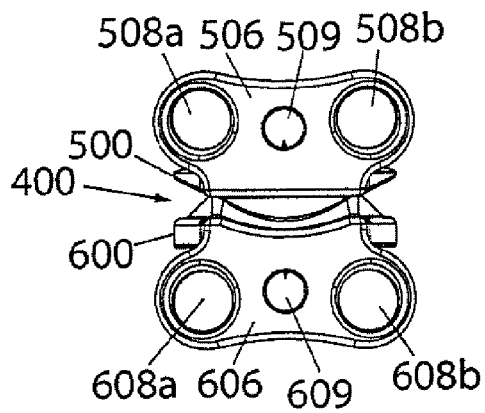
Figure 3D:
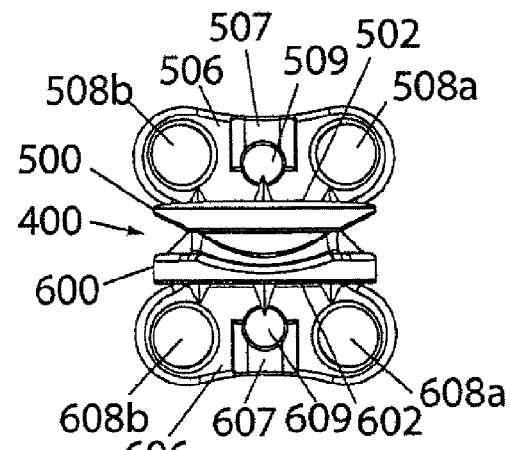
Figure 3E:
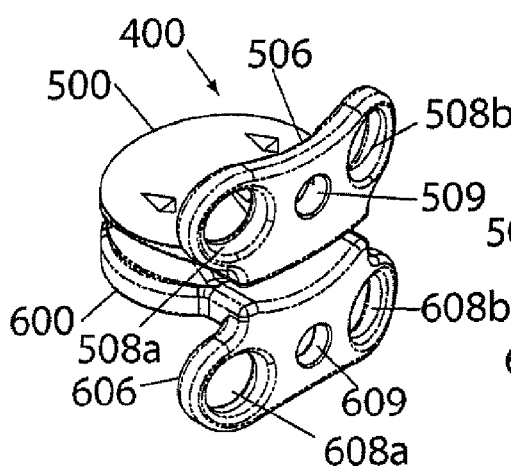
Figure 3F:
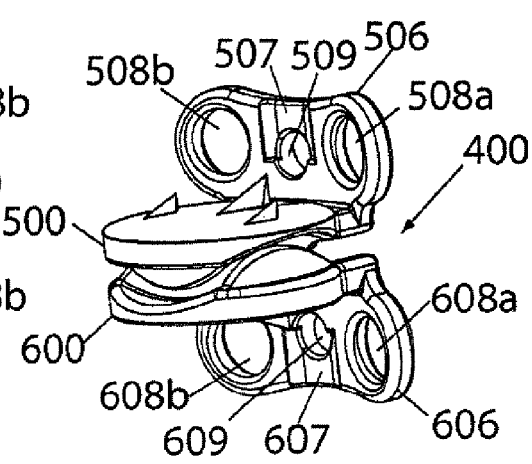
Figure 4A:
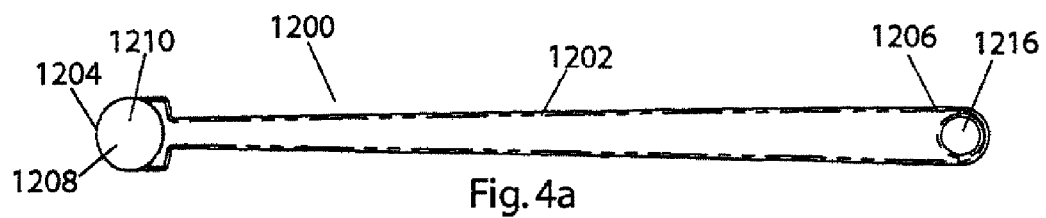
FIGS. 4a-g show top (FIG. 4a), lateral (FIG. 4b), anterior (FIG. 4c), posterior (FIG. 4d), antero-lateral perspective (head only) (FIG. 4e), and postero-lateral perspective (head only) (FIG. 4f) views of a cervical disc replacement trial of the present invention.
Figure 4B:
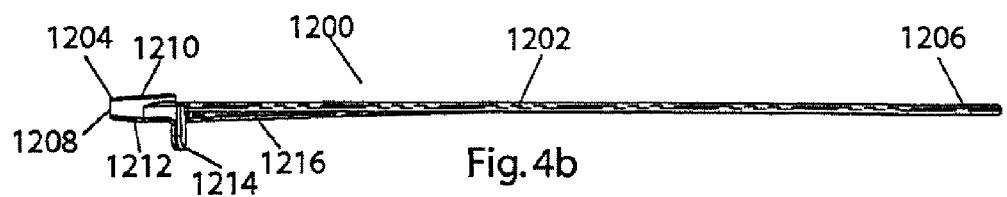
Figures 4C, 4D, 4E:
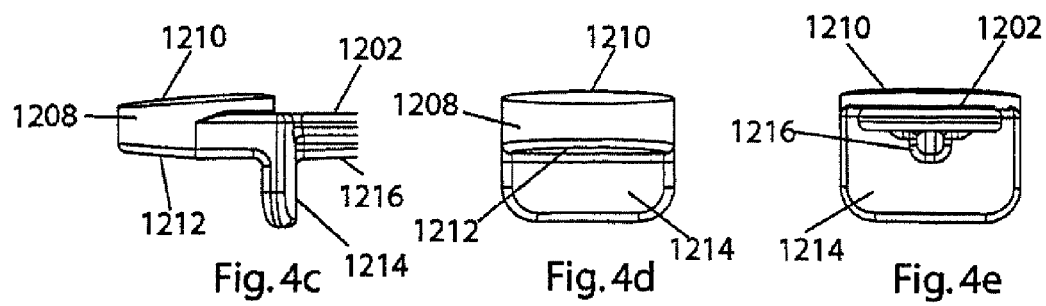
Figures 4F, 4G:
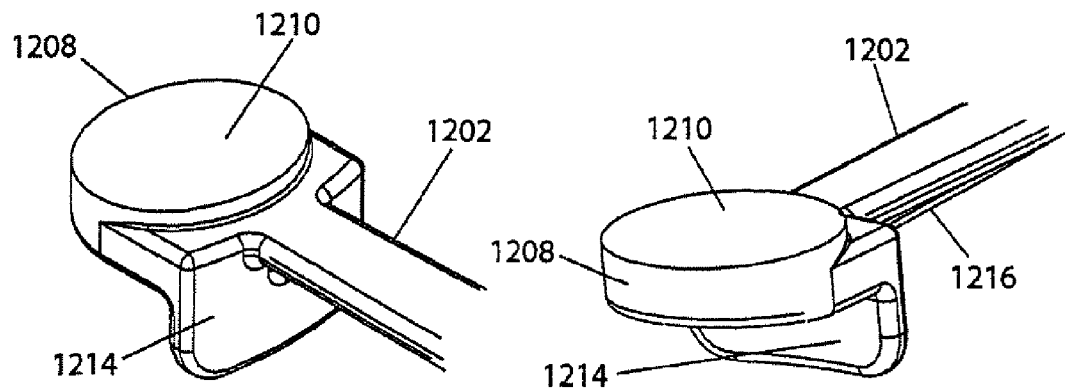

While the invention will be described more fully hereinafter with reference to the accompanying drawings, it is to be understood at the outset that persons skilled in the art may modify the invention herein described while achieving the functions and results of the invention. Accordingly, the descriptions that follow are to be understood as illustrative and exemplary of specific structures, aspects and features within the broad scope of the invention and not as limiting of such broad scope. Like numbers refer to similar features of like elements throughout.

A preferred embodiment of a cervical disc replacement device of the present invention, for use with the instrumentation of the present invention, will now be described.

Referring now to FIGS. 1a-3f, a top element 500 of the cervical disc replacement device 400 is shown in anterior (FIG. 1a), lateral (FIG. 1b), and bottom (FIG. 1c) views; a bottom element 600 of the cervical disc replacement device 400 is shown in anterior (FIG. 2a), lateral (FIG. 2b), and top (FIG. 2c) views; and an assembly 400 of the top and bottom elements 500,600 is shown in top (FIG. 3a), lateral (FIG. 3b), anterior (FIG. 3c), posterior (FIG. 3d), antero-lateral perspective (FIG. 3e), and postero-lateral perspective (FIG. 3f) views.

The cervical disc replacement device 400 is an alternate embodiment of the cervical disc replacement device of the '702 application. The illustrated alternate embodiment of the cervical disc replacement device is identical in structure to the cervical disc replacement device 100 in the '702 application (and thus like components are like numbered, but in the 400s rather than the 100s, in the 500s rather than the 200s, and in the 600s rather than the 300s), with the exception that the vertebral bone attachment flanges are configured differently, such that they are suitable for engagement by the instrumentation described herein. (It should be noted that, while the '702 application illustrated and described the cervical disc replacement device 100 as having an upper element flange 506 with two bone screw holes 508a,508b, and a lower element flange 606 with one bone screw hole 608, the '702 application explained that the number of holes and the configuration of the flanges could be modified without departing from the scope of the invention as described in the '702 application.)

More particularly, in this alternate embodiment, the upper element 500 of the cervical disc replacement device 400 has a vertebral body attachment structure (e.g., a flange) 506 that preferably extends upwardly from the anterior edge of the upper element 500, and preferably has a lateral curvature that approximates the curvature of the anterior periphery of the upper vertebral body against which it is to be secured. The attachment flange 506 is preferably provided with a flat recess 507, centered on the midline, that accommodates a clip 1150a (described below) of the present invention. The attachment flange 506 is further provided with at least one (e.g., two) bone screw holes 508a,508b, preferably symmetrically disposed on either side of the midline. Preferably, the holes 508a,508b have longitudinal axes directed along preferred bone screw driving lines. For example, in this alternate embodiment, the preferred bone screw driving lines are angled upwardly at 5 degrees and inwardly (toward one another) at 7 degrees (a total of 14 degrees of convergence), to facilitate a toenailing of the bone screws (described below and shown in FIGS. 12a-h). Centrally between the bone screw holes 508a,508b, at least one mounting feature (e.g., a mounting screw hole) 509 is provided for attaching the upper element 500 to an insertion plate 700 (described below) for implantation.

Similarly, in this alternate embodiment, the lower element 600 of the cervical disc replacement device 400 also has a vertebral body attachment structure (e.g., an oppositely directed and similarly configured vertebral body attachment flange) 606 that preferably extends downwardly from the anterior edge of the lower element 600, and preferably has a lateral curvature that approximates the curvature of the anterior periphery of the lower vertebral body against which it is to be secured. The attachment flange 606 is preferably provided with a flat recess 607, centered on the midline, that accommodates a clip 1150b (described below) of the present invention. The attachment flange 606 is further provided with at least one (e.g., two) bone screw holes 608a,608b, preferably symmetrically disposed on either side of the midline. Preferably, the holes 608a,608b have longitudinal axes directed along preferred bone screw driving lines. For example, in this alternate embodiment, the preferred bone screw driving lines are angled downwardly at 5 degrees and inwardly (toward one another) at 7 degrees (a total of 14 degrees of convergence), to facilitate a toenailing of the bone screws (described below and shown in FIGS. 12a-h). Centrally between the bone screw holes 608a,608b, at least one mounting feature (e.g., a mounting screw hole) 609 is provided for attaching the lower element 600 to the insertion plate 700 (described below) for implantation.

Prior to implantation of the cervical disc replacement device, the surgeon will prepare the intervertebral space. Typically, this will involve establishing access to the treatment site, removing the damaged natural intervertebral disc, preparing the surfaces of the endplates of the vertebral bones adjacent the intervertebral space, and distracting the intervertebral space. (It should be noted that the cervical disc replacement device of the present invention, and the instrumentation and implantation methods described herein, require minimal if any endplate preparation.) More particularly, after establishing access to the treatment site, the surgeon will remove the natural disc material, preferably leaving as much as possible of the annulus intact. Then, the surgeon will remove the anterior osteophyte that overhangs the mouth of the cervical intervertebral space, and any lateral osteophytes that may interfere with the placement of the cervical disc replacement device or the movement of the joint. Using a burr tool, the surgeon will then ensure that the natural lateral curvature of the anterior faces of the vertebral bodies is uniform, by removing any surface anomalies that deviate from the curvature. Also using the burr tool, the surgeon will ensure that the natural curvature of the endplate surface of the upper vertebral body, and the natural flatness of the endplate surface of the lower vertebral body, are uniform, by removing any surface anomalies that deviate from the curvature or the flatness. Thereafter, the surgeon will distract the intervertebral space to the appropriate height for receiving the cervical disc replacement device. Any distraction tool or method known in the art, e.g., a Caspar Distractor, can be used to effect the distraction and/or hold open the intervertebral space. Additionally or alternatively, the cervical disc replacement trials of the present invention can be used to distract the intervertebral space (as described below).

Referring now to FIGS. 4a-f, a cervical disc replacement trial 1200 of the present invention is shown in top (FIG. 4a), lateral (FIG. 4b), lateral (head only) (FIG. 4c), posterior (FIG. 4d), anterior (FIG. 4e), antero-lateral perspective (head only) (FIG. 4f), and postero-lateral perspective (head only) (FIG. 4g) views.

Preferably, a plurality of cervical disc replacement trials are provided primarily for use in determining the appropriate size of a cervical disc replacement device to be implanted (or whether a particular size of the cervical disc replacement device can be implanted) into the distracted cervical intervertebral space (e.g., the cervical disc replacement device 400 of FIGS. 1a-3f). Preferably, for each cervical disc replacement device to be implanted, a plurality of sizes of the cervical disc replacement device would be available. That is, preferably, a plurality of the same type of cervical disc replacement device would be available, each of the plurality having a respective footprint and depth dimension combination that allows it to fit within a correspondingly dimensioned intervertebral space. For example, the plurality of cervical disc replacement devices could include cervical disc replacement devices having oval footprints being 12 mm by 14 mm, 14 mm by 16 mm, or 16 mm by 18 mm, and depths ranging from 6 mm to 14 mm in 1 mm increments, for a total of 27 devices. Accordingly, preferably, each of the plurality of trials for use with a particular plurality of differently sized cervical disc replacement devices would have a respective oval footprint and depth dimension set corresponding to the footprint and depth dimension set of a respective one of the plurality of differently sized cervical disc replacement devices. For example, the plurality of trials for use with the set of cervical disc replacement devices described, for example, could include trials having oval footprints being 12 mm by 14 mm, 14 mm by 16 mm, or 16 mm by 18 mm, and depths ranging from 6 mm to 14 mm in 1 mm increments, for a total of 27 static trials. It should be understood that the cervical disc replacement devices and/or the trials can be offered in a variety of dimensions without departing from the scope of the invention, and that the dimensions specifically identified and quantified herein are merely exemplary. Moreover, it should be understood that the set of trials need not include the same number of trials for each cervical disc replacement device in the set of cervical disc replacement devices, but rather, none, one, or more than one trial can be included in the trial set for any particular cervical disc replacement device in the set.

Each of the cervical disc replacement trials (the cervical disc replacement trial 1200 shown in FIGS. 4a-g is exemplary for all of the trials in the plurality of trials; preferably the trials in the plurality of trials differ from one another only with regard to certain dimensions as described above) includes a shaft 1202 having a configured distal end 1204 and a proximal end having a handle 1206. Preferably, the proximal end is provided with a manipulation features (e.g., a hole 1216) to, e.g., decrease the weight of the trial 1200, facilitate manipulation of the trial 1200, and provide a feature for engagement by an instrument tray protrusion. The distal end is configured to approximate relevant dimensions of the cervical disc replacement device. More particularly in the illustrated embodiment (for example), the distal end 1204 has a trial configuration (e.g., a head 1208 having an oval footprint dimensioned at 12 mm by 14 mm, and a thickness of 6 mm). The upper surface 1210 of the head 1208 is convex, similar to the configuration of the vertebral body contact surface of the upper element 500 of the cervical disc replacement device 400 (but without the teeth). The lower surface 1212 of the head 1208 is flat, similar to the configuration of the vertebral body contact surface of the lower element 600 of the cervical disc replacement device 400 (but without the teeth). The illustrated embodiment, therefore, with these dimensions, approximates the size of a cervical disc replacement device having the same height and footprint dimensions. The cervical disc replacement trial, not having the teeth, can be inserted and removed from the intervertebral space without compromising the endplate surfaces. The cervical disc replacement trial 1200 further has an over-insertion prevention features (e.g., a vertebral body stop 1214) preferably disposed at the anterior edge of the head 1208, to engage the anterior surface of the upper vertebral body before the trial 1200 is inserted too far into the intervertebral space. The body of the trial 1200 preferably has one or more structural support features (e.g., a rib 1216 extending anteriorly from the head 1208 below the shaft 1202) that provides stability, e.g., to the shaft 1202 for upward and downward movement, e.g., if the head 1208 must be urged into the intervertebral space by moving the shaft 1202 in this manner. Further, preferably as shown, the head 1208 is provided with an insertion facilitation features (e.g., a taper, decreasing posteriorly) to facilitate insertion of the head 1208 into the intervertebral space by, e.g., acting as a wedge to urge the vertebral endplates apart. Preferably, as shown, the upper surface 1210 is fully tapered at approximately 5 degrees, and the distal half of the lower surface 1212 is tapered at approximately 4 degrees.

Accordingly, the surgeon can insert and remove at least one of the trials (or more, as necessary) from the prepared intervertebral space. As noted above, the trials are useful for distracting the prepared intervertebral space. For example, starting with the largest distractor that can be wedged in between the vertebral bones, the surgeon will insert the trial head 1208 (the tapering of the trial head 1208 facilitates this insertion by acting as a wedge to urge the vertebral endplates apart), and then lever the trial handle 1206 up and down to loosen the annulus and surrounding ligaments to urge the bone farther apart. Once the annulus and ligaments have been loosened, the surgeon removes the trial head 1208 from the intervertebral space, and replaces it with the next largest (in terms of height) trial head 1208. The surgeon then levers the trial handle 1206 up and down to further loosen the annulus and ligaments. The surgeon then proceeds to remove and replace the trial head 1208 with the next largest (in terms of height) trial head 1208, and continues in this manner with larger and larger trials until the intervertebral space is distracted to the appropriate height. This gradual distraction method causes the distracted intervertebral space to remain at the distracted height with minimal subsidence before the cervical disc replacement device is implanted. The appropriate height is one that maximizes the height of the intervertebral space while preserving the annulus and ligaments.

Regardless of the distraction method used, the cervical disc replacement trials are useful for finding the cervical disc replacement device size that is most appropriate for the prepared intervertebral space, because each of the trial heads approximates the relevant dimensions of an available cervical disc replacement device. Once the intervertebral space is distracted, the surgeon can insert and remove one or more of the trial heads to determine the appropriate size of cervical disc replacement device to use. Once the appropriate size is determined, the surgeon proceeds to implant the selected cervical disc replacement device.

A preferred method of, and instruments for use in, implanting the cervical disc replacement device will now be described.

Figure 5A:
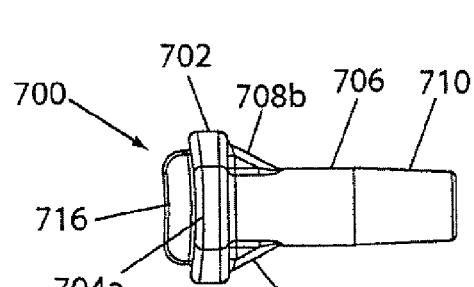
FIGS. 5a-d show top (FIG. 5a), lateral (FIG. 5b), anterior (FIG. 5c), and posterior (FIG. 5d) views of an insertion plate of the insertion instrumentation of the present invention.
Figure 5B:
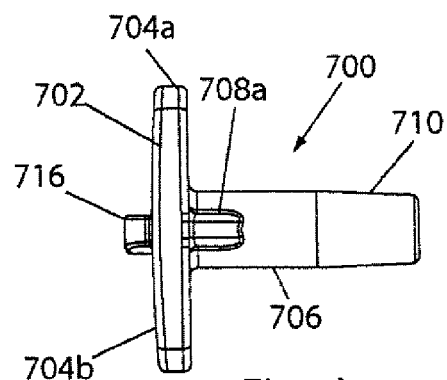
Figure 5C:
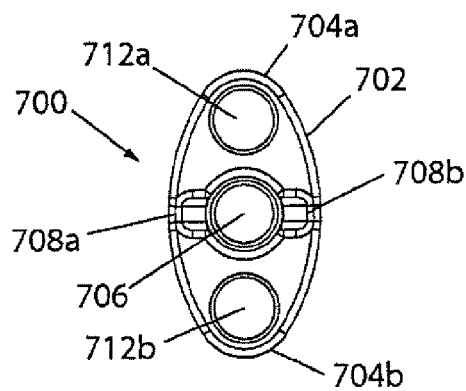
Figure 5D:
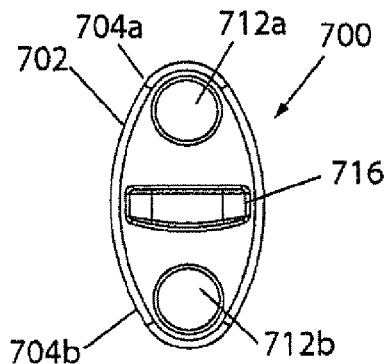
Figure 5E:
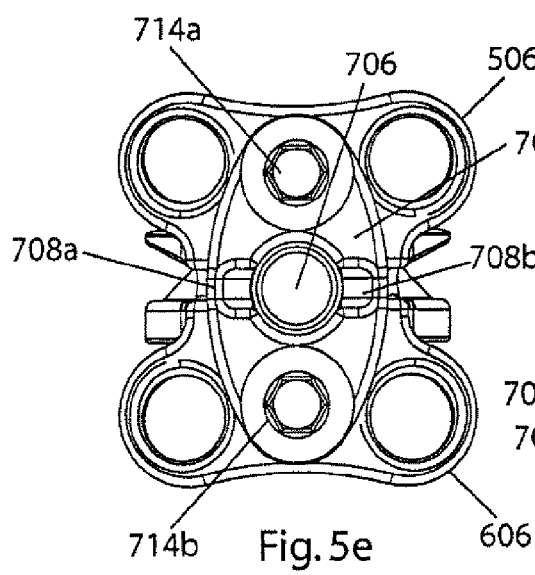
FIGS. 5e and 5f show anterior (FIG. 5e) and antero-lateral perspective (FIG. 5f) views of the insertion plate mounted to the cervical disc replacement device.
Figure 5F:
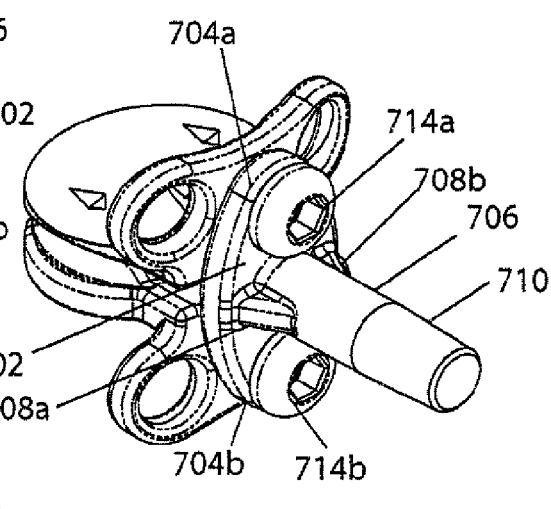

Referring now to FIGS. 5a-f, an insertion plate 700 of the insertion instrumentation of the present invention is shown in top (FIG. 5a), lateral (FIG. 5b), anterior (FIG. 5c), and posterior (FIG. 5d) views. FIGS. 5e and 5f show anterior (FIG. 5e) and antero-lateral perspective (FIG. 5f) views of the insertion plate 700 mounted to the cervical disc replacement device 400.

The insertion plate 700 has a base 702 with a first mounting area 704a (preferably an upwardly extending flange) and a second mounting area 704b (preferably a downwardly extending flange), and a primary attachment feature (e.g., an anteriorly extending central stem) 706. The connection of the stem 706 to the base 702 preferably includes an axial rotation prevention feature, e.g., two oppositely and laterally extending key flanges 708a,708b. The stem 706 preferably has a proximal portion 710 that is tapered to have a decreasing diameter away from the base 702. That is, the tapered proximal portion 710 has an initial smaller diameter that increases toward the base 702 gradually to a final larger diameter. The base 702 preferably has a posteriorly extending ledge 716 that has a flat upper surface and a curved lower surface.

The insertion plate 700 is mounted to the cervical disc replacement device 400 to facilitate the preferred simultaneous implantation of the upper and lower elements 500,600. The upper and lower elements 500,600 are held by the insertion plate 700 in a preferred relationship to one another that is suitable for implantation. More particularly, as shown in FIGS. 3a-f, 5e, and 5f, the elements 500,600 are preferably axially rotationally aligned with one another, with the element perimeters and flanges 506,606 axially aligned with one another, and held with the bearing surfaces 512,612 in contact. The ledge 716 maintains a separation between the anterior portions of the inwardly facing surfaces of the elements 500,600 to help establish and maintain this preferred relationship, with the flat upper surface of the ledge 716 in contact with the flat anterior portion of the inwardly facing surface of the upper element 500, and the curved lower surface of the ledge 716 in contact with the curved anterior portion of the inwardly facing surface of the lower element 600.

While any suitable method or mechanism can be used to mount the elements 500,600 to the insertion plate 700, a preferred arrangement is described. That is, it is preferred, as shown and as noted above, that the flanges 506,606 of the elements 500,600 (in addition to having the bone screw holes 508a,508b,608a,608b described above) each have at least one mounting feature (e.g., mounting screw hole 509,609), and the insertion plate 700 has two (at least two, each one alignable with a respective mounting screw hole 509,609) corresponding mounting features (e.g., mounting screw holes 712a,712b), spaced to match the spacing of (and each be colinear with a respective one of) the mounting screw holes 509,609 on the flanges 506,606 of the elements 500,600 of the cervical disc replacement device 400 when those elements 500,600 are disposed in the preferred relationship for implantation. Accordingly, mounting screws 714a,714b or other suitable fixation devices are secured through the colinear mounting screw hole pairs 509,712a and 609,712b (one screw through each pair), such that the elements 500,600 are immovable with respect to the insertion plate 700 and with respect to one another. Thus, in this configuration, the upper element 500, lower element 600, and insertion plate 700 construct is manipulatable as a single unit.

Preferably, for each size of cervical disc replacement device, the described configuration is established (and rendered sterile in a blister pack through methods known in the art) prior to delivery to the surgeon. That is, as described below, the surgeon will simply need to open the blister pack and apply the additional implantation tools to the construct in order to implant the cervical disc replacement device. Preferably, the configuration or dimensions of the insertion plate can be modified (either by providing multiple different insertion plates, or providing a single dynamically modifiable insertion plate) to accommodate cervical disc replacement devices of varying heights. For example, the positions of the mounting screw holes 712a,712b on the flanges 704a,704b can be adjusted (e.g., farther apart for replacement devices of greater height, and close together for replacement devices of lesser height), and the size of the flanges 704a,70b can be adjusted to provide structural stability for the new hole positions. Preferably, in other respects, the insertion plate configuration and dimensions need not be modified, to facilitate ease of manufacturing and lower manufacturing costs.

It should be noted that the described configuration of the construct presents the cervical disc replacement device to the surgeon in a familiar manner. That is, by way of explanation, current cervical fusion surgery involves placing a fusion device (e.g., bone or a porous cage) in between the cervical intervertebral bones, and attaching a cervical fusion plate to the anterior aspects of the bones. Widely used cervical fusion devices (an example single level fusion plate 1300 is shown in anterior view in FIG. 13a and in lateral view in FIG. 13b) are configured with a pair of laterally spaced bone screw holes 1302a,1302b on an upper end 1304 of the plate 1300, and a pair of laterally spaced bone screw holes 1306a,1306b on a lower end 1308 of the plate 1300. To attach the plate 1300 to the bones, two bone screws are disposed through the upper end's bone screw holes 1302a,1302b and into the upper bone, and two bone screws are disposed through the lower end's bone screw holes 1306a,1306b and into the lower bone. This prevents the bones from moving relative to one another, and allows the bones to fuse to one another with the aid of the fusion device.

Accordingly, as can be seen in FIG. 5e, when the upper and lower elements 500,600 of the cervical disc replacement device 400 are held in the preferred spatial relationship, the flanges 506,606 of the elements 500,600, and their bone screw holes 508a,508b, present to the surgeon a cervical hardware and bone screw hole configuration similar to a familiar cervical fusion plate configuration. The mounting of the elements 500,600 to the insertion plate 700 allows the elements 500,600 to be manipulated as a single unit for implantation (by manipulating the insertion plate 700), similar to the way a cervical fusion plate is manipulatable as a single unit for attachment to the bones. This aspect of the present invention simplifies and streamlines the cervical disc replacement device implantation procedure.

As noted above, the cervical disc replacement device 400 and insertion plate 700 construct is preferably provided sterile (e.g., in a blister pack) to the surgeon in an implant tray (the tray preferably being filled with constructs for each size of cervical disc replacement device). The construct is preferably situated in the implant tray with the stem 706 of the insertion plate 700 facing upwards for ready acceptance of the insertion handle 800 (described below).

Referring now to FIGS. 6a-e, an insertion handle 800 of the insertion instrumentation of the present invention is shown in top (FIG. 6a), lateral (FIG. 6b), anterior (FIG. 6c), and postero-lateral (distal end only) (FIG. 6d) views. FIG. 6e shows an antero-lateral perspective view of the insertion handle 800 attached to the stem 706 of the insertion plate 700. FIG. 6f shows a magnified view of the distal end of FIG. 6e.

The insertion handle 800 is provided primarily for engaging the stem 706 of the insertion plate 700 so that the cervical disc replacement device 400 and insertion plate 700 construct can be manipulated into and within the treatment site. The insertion handle 800 has a shaft 802 with an attachment feature (e.g., a longitudinal bore) 804 at a distal end 806 and a manipulation feature (e.g., a flange) 810 at a proximal end 808. Preferably, the longitudinal bore 804 has an inner taper at the distal end 806 such that the inner diameter of the distal end 806 decreases toward the distal end 806, from an initial larger inner diameter at a proximal portion of the distal end 806 to a final smaller inner diameter at the distal edge of the distal end 806. The distal end 806 also preferably has an axial rotation prevention feature, e.g., two (at least one) key slots 814a,814b extending proximally from the distal end 806. Each slot 814a,814b is shaped to accommodate the key flanges 708a,708b at the connection of the base 702 to the stem 706 when the distal end 806 is engaged with the stem 706. The material from which the insertion handle 800 is formed (preferably, e.g., Ultem™), and also the presence of the key slots 814a,814b, permits the diameter of the hollow distal end 806 to expand as needed to engage the tapered stem 706 of the insertion plate 700. More particularly, the resting diameter (prior to any expansion) of the hollow distal end 806 of the insertion handle 800 is incrementally larger than the initial diameter of the tapered proximal portion 710 of the stem 706 of the insertion plate 700, and incrementally smaller than the final diameter of the tapered proximal portion 710 of the stem 706 of the insertion plate 700. Accordingly, longitudinally aligning the insertion handle shaft 802 with the stem 706, and thereafter pushing the hollow distal end 806 of the insertion handle shaft 802 toward the insertion plate 700, causes the hollow distal end 806 to initially readily encompass the tapered proximal portion 710 of the stem 706 (because the initial diameter of the tapered proximal portion 710 is smaller than the resting diameter of the hollow tapered distal end 806). With continued movement of the insertion handle shaft 802 toward the insertion plate base 702, the hollow distal end 806 is confronted by the increasing diameter of the tapered proximal portion 710. Accordingly, the diameter of the hollow distal end 806 expands (by permission of the shaft 802 body material and the key slots 814a,814b as the slots narrow) under the confrontation to accept the increasing diameter. Eventually, with continued movement under force, the inner surface of the hollow distal end 806 is friction-locked to the outer surface of the tapered proximal portion 710. Each of the key slots 814a,814b straddles a respective one of the key flanges 708a,708b at the connection of the base 702 to the stem 706. This enhances the ability of the insertion handle 800 to prevent rotation of the insertion handle shaft 802 relative to the insertion plate 700 (about the longitudinal axis of the insertion handle shaft 802). It should be understood that other methods or mechanisms of establishing engagement of the stem 706 by the insertion handle 800 can be used without departing from the scope of the invention.

Once the insertion handle 800 is engaged with the insertion plate 700, manipulation of the insertion handle shaft 802 effects manipulation of the cervical disc replacement device 400 and insertion plate 700 construct. The surgeon can therefore remove the construct from the implant tray, and insert the construct into the treatment area. More particularly, according to the implantation procedure of the invention, after the surgeon properly prepares the intervertebral space (removes the damaged natural disc, modifies the bone surfaces that define the intervertebral space, and distracts the intervertebral space to the appropriate height), the surgeon inserts the cervical disc replacement device 400 into the intervertebral space from an anterior approach, such that the upper and lower elements 500,600 are inserted between the adjacent vertebral bones with the element footprints fitting within the perimeter of the intervertebral space and with the teeth of the elements' vertebral body contact surfaces 502,602 engaging the vertebral endplates, and with the flanges 506,606 of the upper and lower elements 500,600 flush against the anterior faces of the upper and lower vertebral bones, respectively. (As discussed above, the flanges 506,606 preferably have a lateral curvature that approximates the lateral curvature of the anterior faces of the vertebral bones.)

Figure 7A:
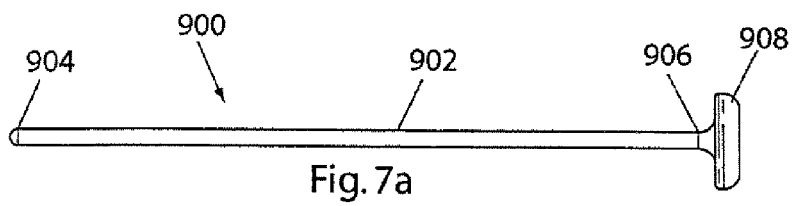
FIGS. 7a-c show top (FIG. 7a), lateral (FIG. 7b), and anterior (FIG. 7c) views of an insertion pusher of the insertion instrumentation of the present invention.
Figure 7B:
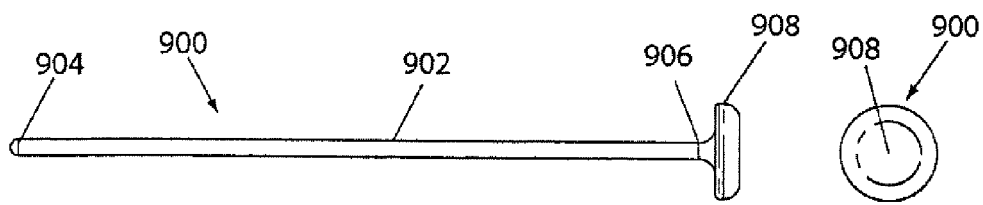
Figure 7C:
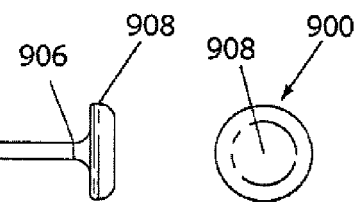
Figure 7D:
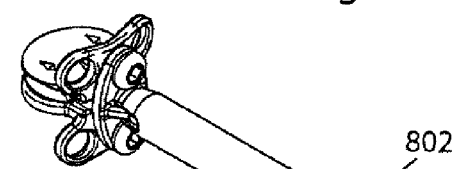
FIG. 7d shows an antero-lateral perspective view of the insertion pusher inserted into the insertion handle.
Figure 7E:
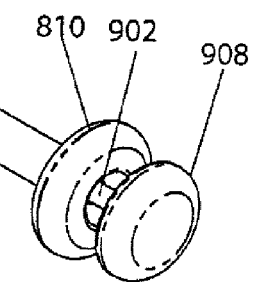
FIG. 7e shows a magnified view of the proximal end of FIG. 7d.

Referring now to FIGS. 7a-e, an insertion pusher 900 of the insertion instrumentation of the present invention is shown in top (FIG. 7a), lateral (FIG. 7b), and anterior (FIG. 7c) views. FIG. 7d shows an antero-lateral perspective view of the insertion pusher 900 inserted into the insertion handle 800. FIG. 7e shows a magnified view of the proximal end of FIG. 7d.

Once the construct is properly positioned in the treatment area, the surgeon uses the insertion pusher 900 to disengage the insertion handle shaft 802 from the stem 706 of the insertion plate 700. More particularly, the insertion pusher 900 has a longitudinal shaft 902 having a preferably blunt distal end 904 and a proximal end 906 preferably having a flange 908. The shaft 902 of the insertion pusher 900 has a diameter smaller than the inner diameter of the insertion handle shaft 802, such that the shaft 902 of the insertion pusher 900 can be inserted into and translated within the longitudinal bore 804 of the insertion handle shaft 802. (The longitudinal bore 804 preferably, for the purpose of accommodating the insertion pusher 900 and other purposes, extends the length of the insertion handle shaft 802.) The shaft 902 of the insertion pusher 900 is preferably as long as (or, e.g., at least as long as) the longitudinal bore 804. Accordingly, to remove the insertion handle shaft 802 from the insertion plate 700, the shaft 902 of the insertion pusher 900 is inserted into the longitudinal bore 804 of the insertion handle shaft 802 and translated therein until the blunt distal end 904 of the pusher shaft 802 is against the proximal end of the tapered stem 706 of the insertion plate 700. Because the shaft 902 of the insertion pusher 900 is as long as the longitudinal bore 804 of the insertion handle shaft 802, the flange 810 of the insertion handle 800 and the flange 908 of the insertion pusher 900 are separated by a distance (see FIGS. 7d and 7e) that is equivalent to the length of that portion of the stem 706 that is locked in the distal end 806 of the insertion handle shaft 802. Accordingly, a bringing together of the flanges 810,908 (e.g., by the surgeon squeezing the flanges 810,908 toward one another) will overcome the friction lock between the distal end 806 of the insertion handle shaft 802 and the stem 706 of the insertion plate 700, disengaging the insertion handle shaft 802 from the insertion plate 700 without disturbing the disposition of the cervical disc replacement device 400 and insertion plate 700 construct in the treatment area.

Referring now to FIGS. 8a-e, a drill guide 1000 of the insertion instrumentation of the present invention is shown in top (FIG. 8a), lateral (FIG. 8b), and anterior (FIG. 8c) views. FIG. 8d shows an antero-lateral perspective view of the drill guide 1000 inserted onto the stem 706 of the insertion plate 700. FIG. 8e shows a magnified view of the distal end of FIG. 8d.

Once the insertion handle 800 has been removed, the surgeon uses the drill guide 1000 to guide the surgeon's drilling of the bone screws (described below) through the bone screw holes 508a,508b and 608a,608b of the upper 500 and lower 600 elements' flanges 506,606 and into the vertebral bones. More particularly, the drill guide 1000 has a longitudinal shaft 1002 having a configured distal end 1004 and a proximal end 1006 with a manipulation feature (e.g., lateral extensions 1008a,1008b). The lateral extensions 1008a,1008b are useful for manipulating the shaft 1002. The distal end 1004 is configured to have a shaft guiding feature (e.g., a central bore 1010) suitable for guiding the shaft 1002 in relation to the stem 706 of the insertion plate 700 therethrough. For example, the central bore 1010 accommodates the stem 706 so that the drill guide 1000 can be placed on and aligned with the stem 706. The longitudinal axis of the bore 1010 is preferably offset from the longitudinal axis of the drill guide shaft 1002. The distal end 1004 is further configured to have two guide bores 1012a,1012b that have respective longitudinal axes at preferred bone screw drilling paths relative to one another. More particularly, the central bore 1010, drill guide shaft 1002, and guide bores 1012a,1012b, are configured on the distal end 1004 of the drill guide 1000 such that when the central bore 1010 is disposed on the stem 706 of the insertion plate 700 (see FIGS. 8d and 8e), the drill guide shaft 1002 can be rotated on the stem 706 into either of two preferred positions in which the guide bores 1012a,1012b are aligned with the bone screw holes 508a,508b or 608a,608b on either of the flanges 506 or 606. Stated alternatively, in a first preferred position (see FIGS. 8d and 8e), the drill guide 1000 can be used to guide bone screws through the bone screw holes 508a,508b in the flange 506 of the upper element 500, and in a second preferred position (in which the drill guide is rotated 180 degrees, about the longitudinal axis of the stem 706, from the first preferred position), the same drill guide 1000 can be used to guide bone screws through the bone screw holes 608a,608b in the flange 606 of the lower element 600. When the drill guide 1000 is disposed in either of the preferred positions, the longitudinal axes of the guide bores 1012a, 1012b are aligned with the bone screw holes 508a,508b or 608a,608b on the flanges 506 or 606, and are directed along preferred bone screw drilling paths through the bone screw holes.

Accordingly, to secure the upper element flange 506 to the upper vertebral body, the surgeon places the drill guide shaft 1002 onto the stem 706 of the insertion plate 700, and rotates the drill guide 1000 into the first preferred position. Preferably, the surgeon then applies an upward pressure to the drill guide 1000, urging the upper element 500 tightly against the endplate of the upper vertebral body. Using a suitable bone drill and cooperating drill bit, the surgeon drills upper tap holes for the upper bone screws. Once the upper tap holes are drilled, the surgeon rotates the drill guide shaft 1002 on the stem 706 of the insertion plate 700 until the guide bores 1012a,1012b no longer cover the upper bone screw holes 508a,508b. The surgeon can then screw the upper bone screws into the upper tap holes using a suitable surgical bone screw driver.

Additionally, to secure the lower element flange 606 to the lower vertebral body, the surgeon further rotates the drill guide shaft 1002 on the stem 706 of the insertion plate 700 until the drill guide 1000 is in the second preferred position. Preferably, the surgeon then applies a downward pressure to the drill guide 1000, urging the lower element 600 tightly against the endplate of the lower vertebral body. Using the suitable bone drill and cooperating drill bit, the surgeon drills lower tap holes for the lower bone screws. Once the lower tap holes are drilled, the surgeon rotates the drill guide shaft 1002 on the stem 706 of the insertion plate 700 until the guide bores 1012a,1012b no longer cover the lower bone screw holes 608a,608b. The surgeon can then screw the lower bone screws into the lower tap holes using the suitable surgical bone screw driver.

It should be noted that the bone screws (or other elements of the invention) may include features or mechanisms that assist in prevent screw backup. Such features may include, but not be limited to, one or more of the following: titanium plasma spray coating, bead blasted coating, hydroxylapetite coating, and grooves on the threads.

Figure 9A:
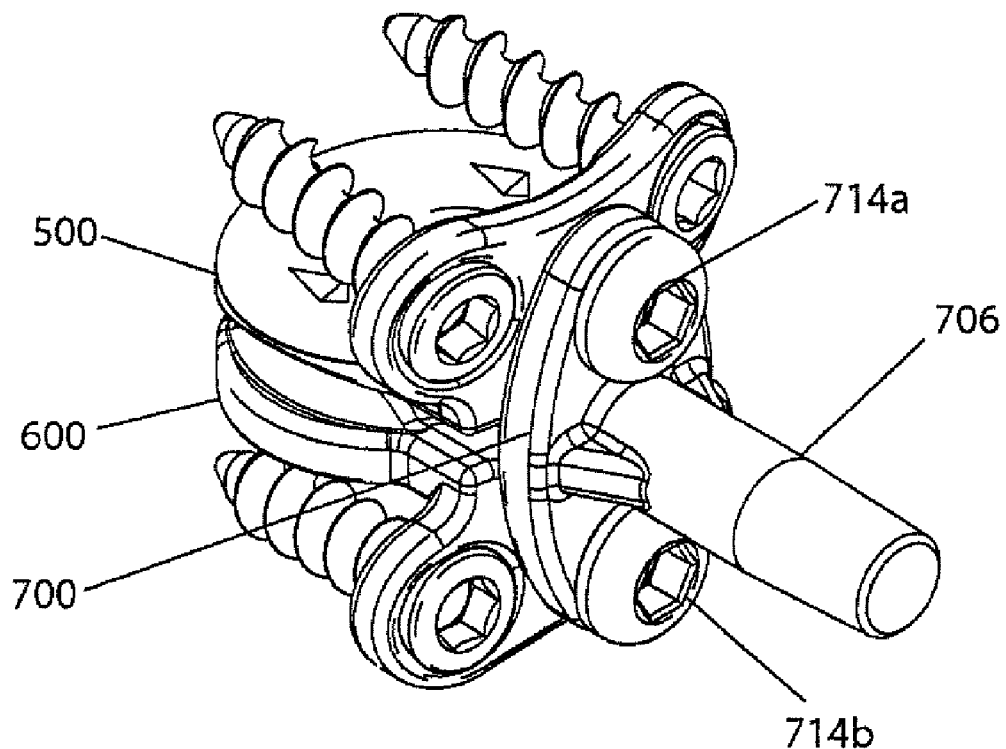
FIG. 9a shows an antero-lateral perspective view of the cervical disc replacement device implantation after bone screws have been applied and before the insertion plate has been removed.
Figure 9B:
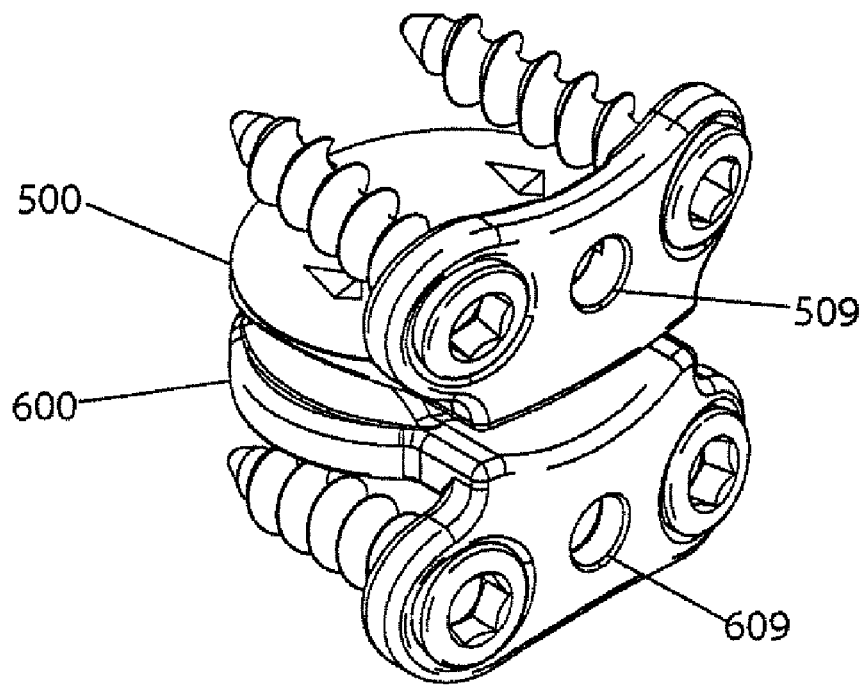
FIG. 9b shows an antero-lateral perspective view of the cervical disc replacement device after bone screws have been applied and after the insertion plate has been removed.
Figure 10A:
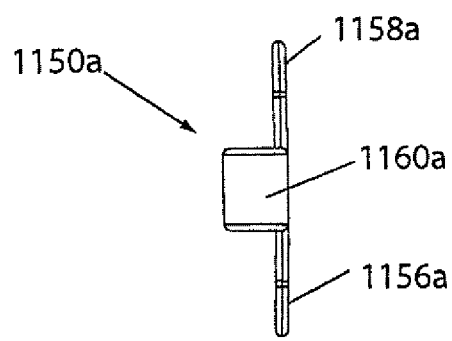
FIGS. 10a-f show top (FIG. 10a), lateral (FIG. 10b), posterior (FIG. 10c), anterior (FIG. 10d), postero-lateral (FIG. 10e), and antero-lateral (FIG. 10f) views of a retaining clip of the present invention.
Figure 10B:
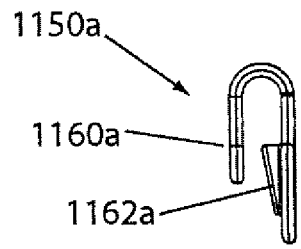
Figure 10C:
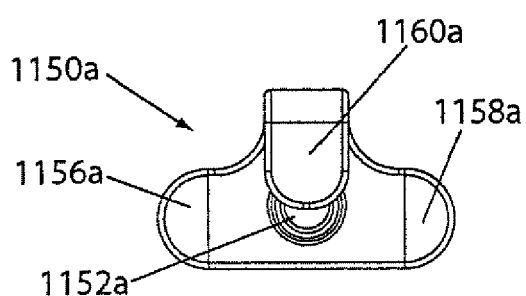
Figure 10D:
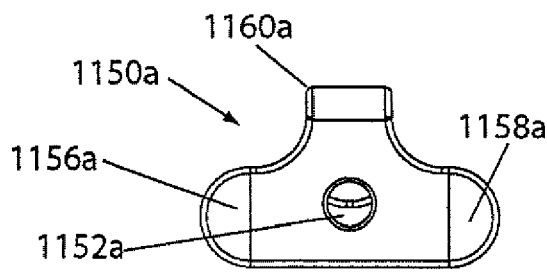
Figure 10E:
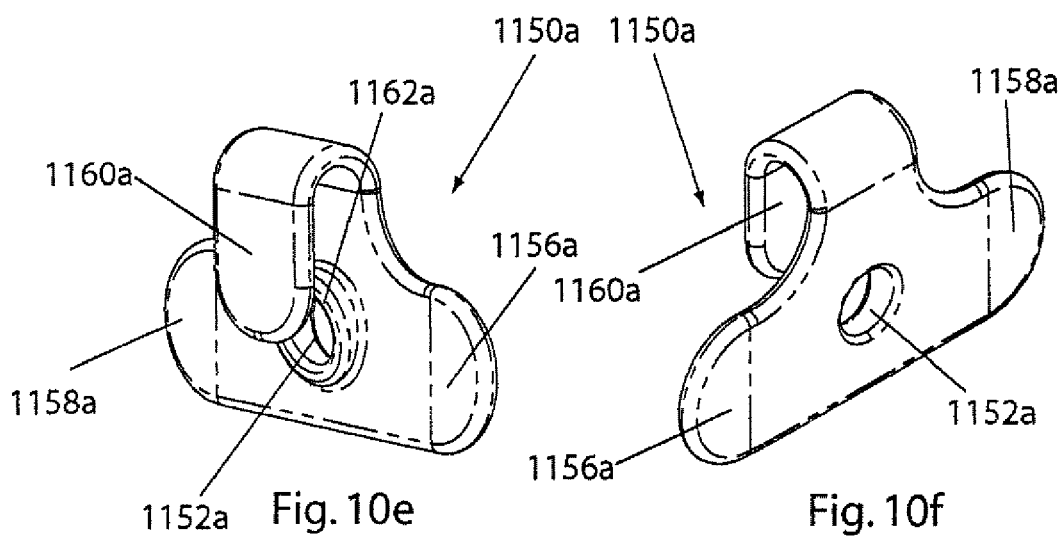
Figure 10F:
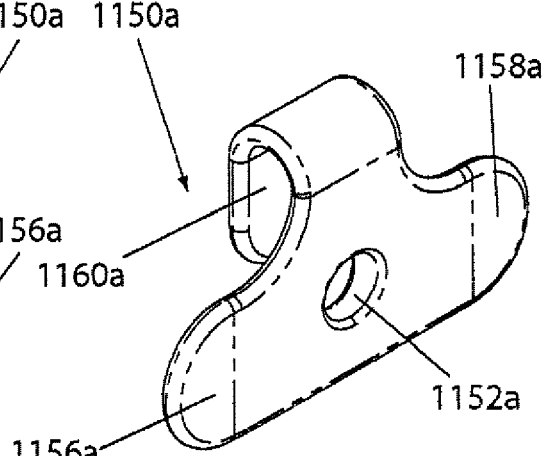

Once the elements 500,600 are secured to the adjacent vertebral bones, the surgeon removes the drill guide 1000 from the stem 706 of the insertion plate 700 and from the treatment area (see FIG. 9a). Using a suitable surgical screw driver, the surgeon then removes the mounting screws 714a, 714b that hold the insertion plate 700 against the elements' flanges 506,606, and removes the insertion plate 700 and the mounting screws 714a,714b from the treatment area (see FIG. 9b).

Figure 11A:
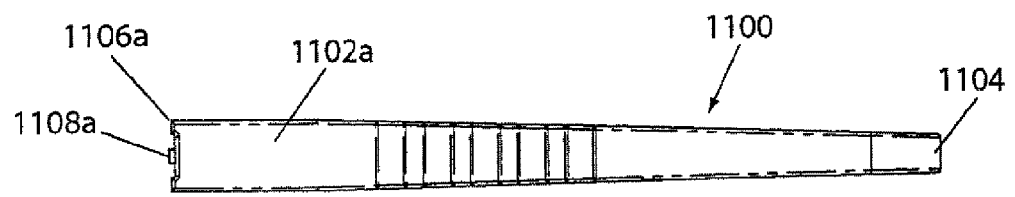
FIGS. 11a-c show top (FIG. 11a), lateral (FIG. 11b), and anterior (FIG. 11c) views of a clip applicator of the insertion instrumentation of the present invention.
Figure 11B:
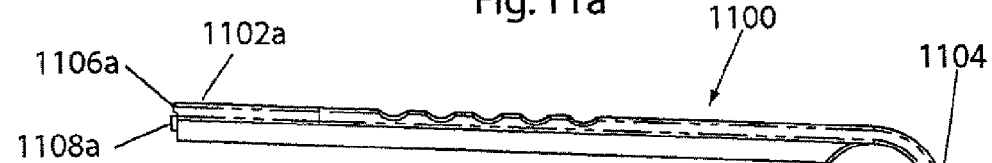
Figure 11C:
Figure 11D:
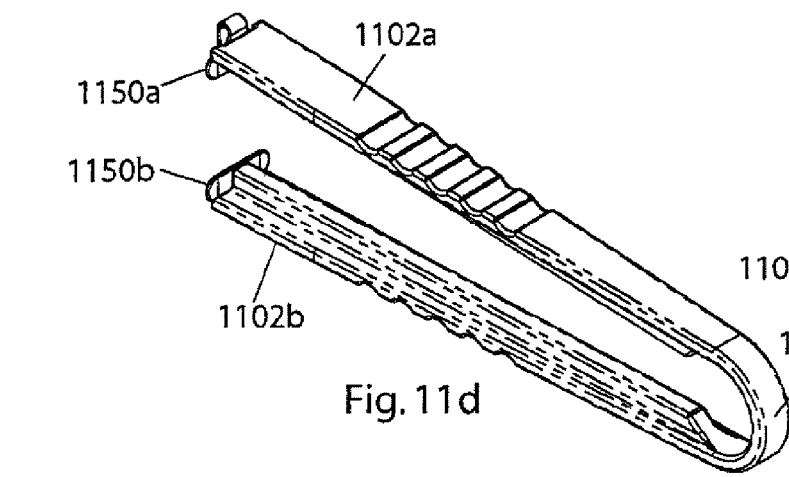
FIG. 11d shows a postero-lateral perspective view of the clip applicator holding two retaining clips.
Figure 11E:
FIG. 11e shows an antero-lateral perspective view of FIG. 11d.
Figure 12A:
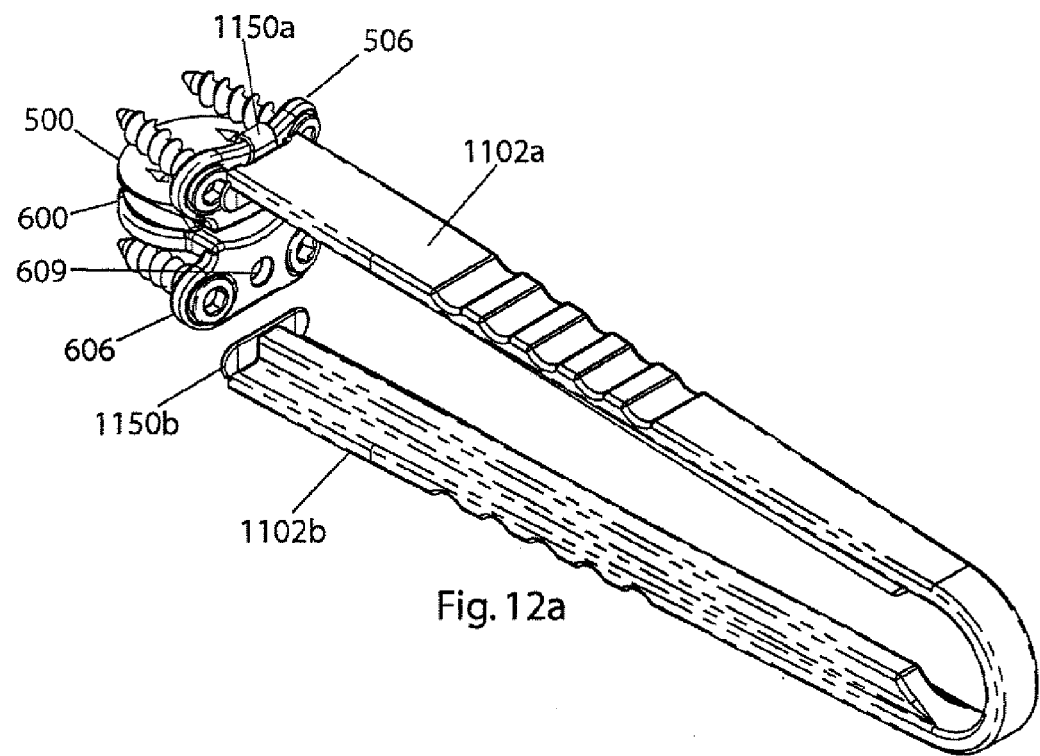
FIG. 12a shows the clip applicator applying the retaining clips to the cervical disc replacement device.
Figures 12B, 12C:
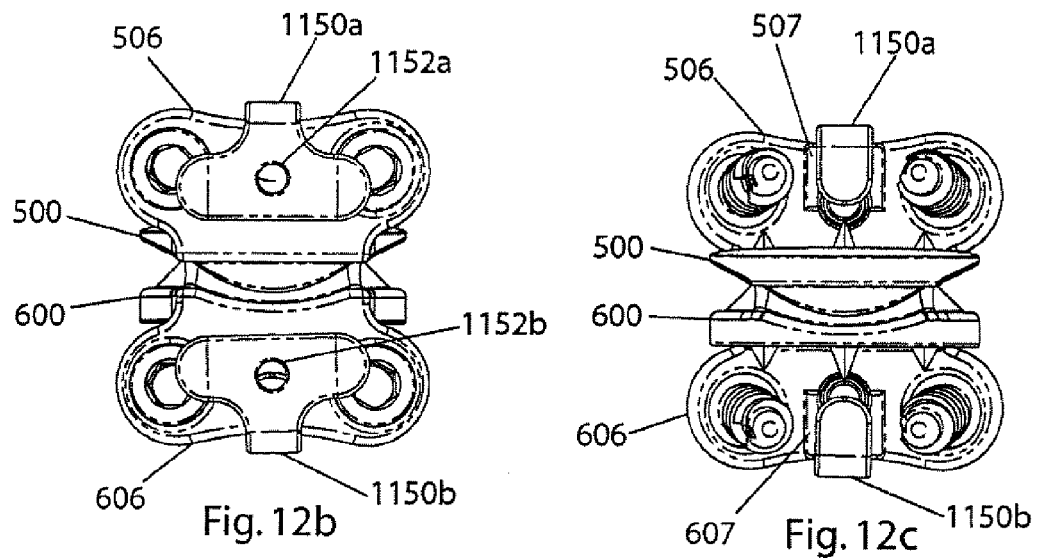

Referring now to FIGS. 10a-f, a retaining clip 1150a of the present invention is shown in top (FIG. 10a), lateral (FIG. 10b), posterior (FIG. 10c), anterior (FIG. 10d), postero-lateral perspective (FIG. 10e), and antero-lateral perspective (FIG. 10f) views. (The features of retaining clip 1150a are exemplary of the features of the like-numbered features of retaining clip 1150b, which are referenced by b's rather than a's.) Referring now to FIGS. 11a-e, a clip applicator 1100 of the insertion instrumentation of the present invention is shown in top (FIG. 11a), lateral (FIG. 11b), and anterior (FIG. 11c) views. FIG. 11d shows a postero-lateral perspective view of the clip applicator 1100 holding two retaining clips 1150a,1150b of the present invention. FIG. 11e shows an antero-lateral perspective view of FIG. 11d. Referring now to FIGS. 12a-h, the clip applicator 1100 is shown applying the retaining clips 1150a,1150b to the cervical disc replacement device 400. FIGS. 12b-h show anterior (FIG. 12b), posterior (FIG. 12c), top (FIG. 12d), bottom (FIG. 12e), lateral (FIG. 12f), antero-lateral perspective (FIG. 12g), and postero-lateral perspective (FIG. 12h) views of the cervical disc replacement device 400 after the retaining clips 1150a,1150b have been applied.

Once the mounting screws 714a,714b and the insertion plate 700 are removed, the surgeon uses the clip applicator 1100 to mount the retaining clips 1150a,1150b on the flanges 506,606 to assist in retaining the bone screws. As shown in FIGS. 10a-f, each of the clips 1150a,1150b preferably has an applicator attachment feature (e.g., a central attachment bore 1152a,1152b) and, extending therefrom, a pair of bone screw retaining features (e.g., oppositely directed laterally extending flanges 1156a,1156b and 1158a,1158b) and a flange attachment feature (e.g., an upwardly (or downwardly) extending hooked flange 1160a,1160b). The extent of the hook flange 1160a,1160b is preferably formed to bend in toward the base of the hook flange 1160a,1160b, such that the enclosure width of the formation is wider than the mouth width of the formation, and such that the extent is spring biased by its material composition toward the base. The enclosure width of the formation accommodates the width of the body of a flange 506,606 of the cervical disc replacement device 400, but the mouth width of the formation is smaller than the width of the flange 506,606. Accordingly, and referring now to FIGS. 12b-h, each clip 1150a,1150b can be applied to an element flange 506,606 such that the hook flange 1160a,1160b grips the element flange 506,606, by pressing the hook's mouth against the edge of the element flange 506,606 with enough force to overcome the bias of the hook flange's extent toward the base, until the flange 506,606 is seated in the hook's enclosure. The attachment bore 1152a, 1152b of the clip 1150a,1150b is positioned on the clip 1150a,1150b such that when the clip 1150a,1150b is properly applied to the flange 506,606, the attachment bore 1152a, 1152b is aligned with the mounting screw hole 509,609 on the flange 506,606 (see FIGS. 12b-h). Further, the posterior opening of the attachment bore 1152a,1152b is preferably surrounded by a clip retaining features (e.g., a raised wall 1162a,1162b), the outer diameter of which is dimensioned such that the raised wall 1162a,1162b fits into the mounting screw hole 509,609 on the element flange 506,606. Thus, when the clip 1150a,1150b is so applied to the element flange 506,606, the element flange 506,606 will be received into the hook's enclosure against the spring bias of the hook's extent, until the attachment bore 1152a,1152b is aligned with the mounting screw hole 509,609, at which time the raised wall 1162a,1162b will snap into the mounting screw hole 509,609 under the force of the hook's extent's spring bias. This fitting prevents the clip 1150a,1150b from slipping off the flange 506,606 under stresses in situ. Each of the laterally extending flanges 1156a,1156b and 1158a,1158b of the clip 1150a, 1150b is sized to cover at least a portion of a respective one of the bone screw heads when the clip 1150a,1150b is attached in this manner to the flange 506,606 (see FIGS. 12b-h), so that, e.g., the clips 1150a,1150b help prevent the bone screws from backing out.

Referring again to FIGS. 11a-e, the clip applicator 1100 has a pair of tongs 1102a,1102b hinged at a proximal end 1104 of the clip applicator 1100. Each tong 1102a,1102b has an attachment feature (e.g., a nub 1108a,1108b) at a distal end 1106a,1106b. Each nub 1108a,1108b is dimensioned such that it can be manually friction locked into either of the attachment bores 1152a,1152b of the retaining clips 1150a, 1150b. Thus, both clips 1150a,1150b can be attached to the clip applicator 1100, one to each tong 1102a,1102b (see FIGS. 11d and 11e). Preferably, as shown in FIGS. 11d and 11e, the clips 1150a,1150b are attached so that their hook flanges 1154a,1154b are directed toward one another, so that they are optimally situated for attachment to the element flanges 506,606 of the cervical disc replacement device 400 (see FIG. 12a).

Preferably, the clips 1150a,1150b are attached to the clip applicator 1100 as described above prior to delivery to the surgeon. The assembly is preferably provided sterile to the surgeon in a blister pack. Accordingly, when the surgeon is ready to mount the clips 1150a,1150b to the element flanges 506,606 of the cervical disc replacement device 400, the surgeon opens the blister pack and inserts the tongs 1102a, 1102b of the clip applicator 1100 (with the clips 1150a,1150b attached) into the treatment area.

Accordingly, and referring again to FIGS. 12a-h, the clips 1150a,1150b can be simultaneously clipped to the upper 500 and lower 600 elements' flanges 506,606 (one to each flange 506,606) using the clip applicator 1100. More particularly, the mouths of the clips 1150a,1150b can be brought to bear each on a respective one of the flanges 506,606 by manually squeezing the tongs 1102a,1102b (having the clips 1150a, 1150b attached each to a set of the distal ends of the tongs 1102a,1102b) toward one another when the mouths of the clips 1150a,1150b are suitably aligned with the flanges 506, 606 (see FIG. 12a). Once the clips 1150a,1150b have been attached to the flanges 506,660 with the raised walls 1162a, 1162b fitting into the mounting screw holes 509,609 of the flanges 506,606, the clip applicator 1100 can be removed from the clips 1150a,1150b by manually pulling the nubs 1108a,1108b out of the attachment bores 1152a,1152b, and the clip applicator 1100 can be removed from the treatment area.

After implanting the cervical disc replacement device 400 as described, the surgeon follows accepted procedure for closing the treatment area.

Figure 15A:
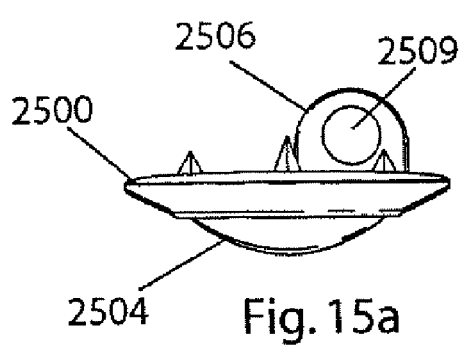
FIGS. 15a-c show an alternate upper element of the configuration of FIGS. 14a-e, in posterior (FIG. 15a), anterior (FIG. 15b), and antero-lateral (FIG. 15c) views.
Figure 15B:
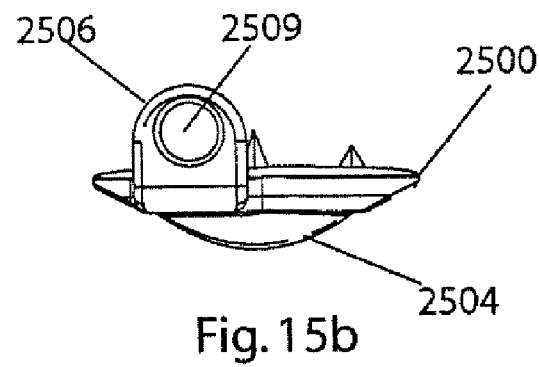
Figure 15C:
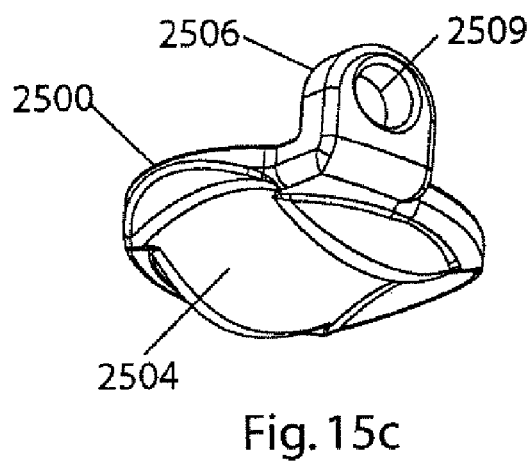
Figure 16C:
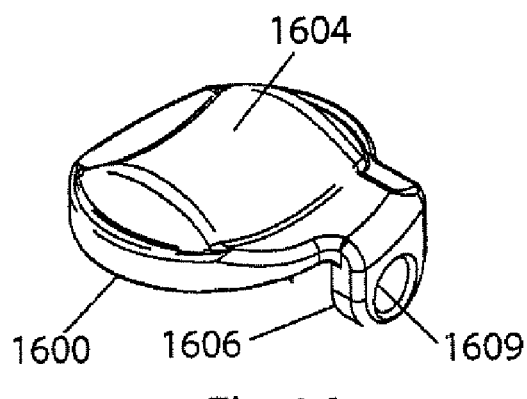
FIGS. 16a-c show an alternate lower element of the configuration of FIGS. 14a-e, in posterior (FIG. 16a), anterior (FIG. 16b), and antero-lateral (FIG. 16c) views.
Figure 16A:
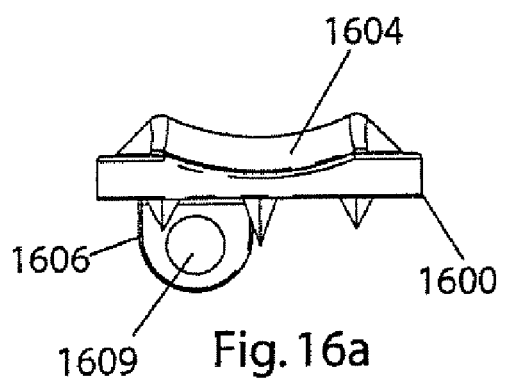
Figure 16B:
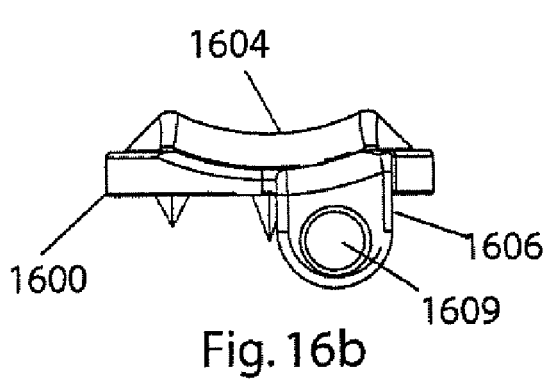
Figure 17A:
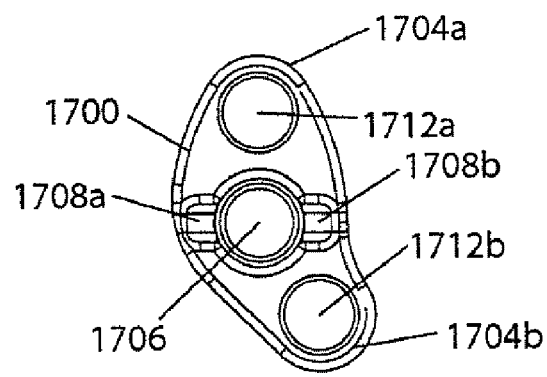
FIGS. 17a-c show an alternate, upper, insertion plate of the configuration of FIGS. 14a-e in anterior (FIG. 17a), posterior (FIG. 17b), and antero-lateral (FIG. 17c) views.
Figure 17B:
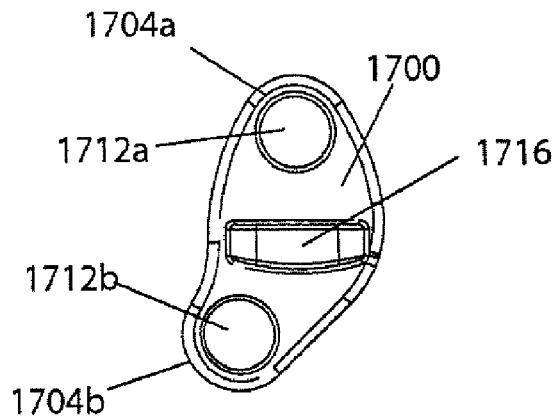
Figure 17C:
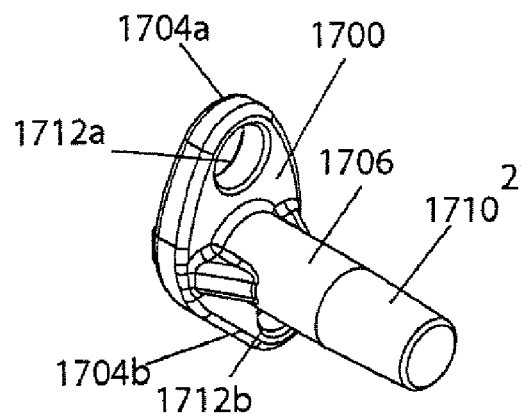
Figure 18C:
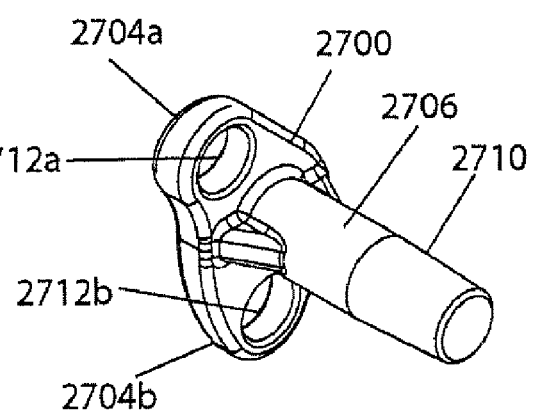
FIGS. 18a-c show an alternate, lower, insertion plate of the configuration of FIGS. 14a-e in anterior (FIG. 18a), posterior (FIG. 18b), and antero-lateral (FIG. 18c) views.
Figure 18A:
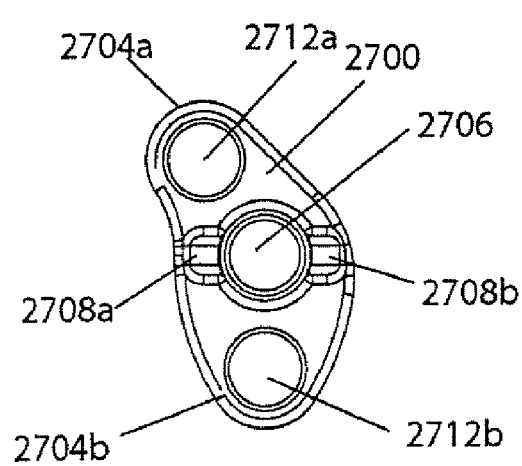
Figure 18B:
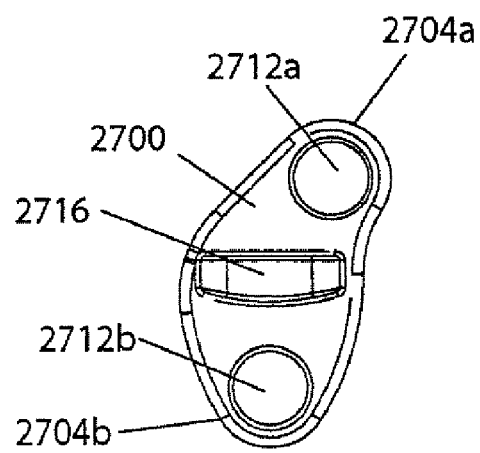

Referring now to FIGS. 14a-e, an alternate dual cervical disc replacement device configuration and alternate insertion plates for use therewith, suitable, for example, for implantation in two adjacent cervical intervertebral spaces, are illustrated in exploded perspective (FIG. 14a), anterior (FIG. 14b), posterior (FIG. 14c), lateral (FIG. 14d), and collapsed perspective (FIG. 14e) views. Referring now also to FIGS. 15a-c, an alternate upper element of the configuration is shown in posterior (FIG. 15a), anterior (FIG. 15b), and antero-lateral (FIG. 15c) views. Referring now also to FIGS. 16a-c, an alternate lower element of the configuration is shown in posterior (FIG. 16a), anterior (FIG. 16b), and antero-lateral (FIG. 16c) views. Referring now also to FIGS. 17a-c, an alternate, upper, insertion plate of the configuration is shown in anterior (FIG. 17a), posterior (FIG. 17b), and antero-lateral (FIG. 17c) views. Referring now also to FIGS. 18a-c, an alternate, lower, insertion plate of the configuration is shown in anterior (FIG. 18a), posterior (FIG. 18b), and antero-lateral (FIG. 18c) views.

More particularly, the alternate dual cervical disc replacement device configuration 1350 is suitable, for example, for implantation into two adjacent cervical intervertebral spaces. The configuration preferably, as shown, includes an alternate, upper, cervical disc replacement device 1400 (including an upper element 1500 and an alternate, lower, element 1600), for implantation into an upper cervical intervertebral space, and further includes an alternate, lower, cervical disc replacement device 2400 (including an alternate, upper, element 2500 and a lower element 2600), for implantation into an adjacent, lower, cervical intervertebral space. The illustrated alternate, upper, embodiment of the cervical disc replacement device is identical in structure to the cervical disc replacement device 400 described above (and thus like components are like numbered, but in the 1400s rather than the 400s, in the 1500s rather than the 500s, and in the 1600s rather than the 600s), with the exception that the flange 1606 of the lower element 1600 is configured differently and without bone screw holes. The illustrated alternate, lower, embodiment of the cervical disc replacement device is identical in structure to the cervical disc replacement device 400 described above (and thus like components are like numbered, but in the 2400s rather than the 400s, in the 2500s rather than the 500s, and in the 2600s rather than the 600s), with the exception that the flange 2506 of the upper element 2500 is configured differently and without bone screw holes.

More particularly, in the alternate, upper, cervical disc replacement device 1400 of this alternate configuration, the flange 1606 of the lower element 1600 does not have bone screw holes, but has at least one mounting feature (e.g., a mounting screw hole) 1609 for attaching the lower element 1600 to the alternate, upper, insertion plate 1700 (described below). Similarly, and more particularly, in the alternate, lower, cervical disc replacement device 2400 of this alternate configuration, the flange 2506 of the upper element 2500 does not have bone screw holes, but has at least one mounting feature (e.g., a mounting screw hole) 2509 for attaching the upper element 2500 to the alternate, lower, insertion plate 2700 (described below). As can be seen particularly in FIGS. 14a-c, 15b, 16b, 17a, and 18a, the extent of the flange 1606 is laterally offset to the right (in an anterior view) from the midline (and preferably limited to support only the mounting screw hole 1609), and the extent of the flange 2506 is laterally offset to the left (in an anterior view) from the midline (and preferably limited to support only the mounting screw hole 2509), so that the flanges 1606,2506 avoid one another when the alternate lower element 1600 of the alternate, upper, cervical disc replacement device 1400, and the alternate upper element 2500 of the alternate, lower, cervical disc replacement device 2400, are implanted in this alternate configuration (FIGS. 14a-e).

It should be noted that the alternate, upper, cervical disc replacement device 1400 does not require both elements 1500,1600 to be secured to a vertebral body. Only one need be secured to a vertebral body, because due to natural compression in the spine pressing the elements' bearing surfaces together, and the curvatures of the saddle-shaped bearing surfaces preventing lateral, anterior, or posterior movement relative to one another when they are compressed against one another, if one element (e.g., the upper element 1500) is secured to a vertebral body (e.g., to the upper vertebral body by bone screws through the bone screw holes 1508a,1508b of the element flange 1506), the other element (e.g., the alternate, lower, element 1600) cannot slip out of the intervertebral space, even if that other element is not secured to a vertebral body (e.g., to the middle vertebral body). Similarly, the alternate, lower, cervical disc replacement device 2400 does not require both elements 2500,2600 to be secured to a vertebral body. Only one need be secured to a vertebral body, because due to natural compression in the spine pressing the elements' bearing surfaces together, and the curvatures of the saddle-shaped bearing surfaces preventing lateral, anterior, or posterior movement relative to one another when they are compressed against one another, if one element (e.g., the lower element 2600) is secured to a vertebral body (e.g., to the lower vertebral body by bone screws through the bone screw holes 2608a,2608b of the element flange 2606), the other element (e.g., the alternate, upper, element 2500) cannot slip out of the intervertebral space, even if that other element is not secured to a vertebral body (e.g., to the middle vertebral body).

Accordingly, the alternate, upper, insertion plate 1700 is provided to facilitate a preferred simultaneous implantation of the upper and lower elements 1500,1600 of the alternate, upper, cervical disc replacement device 1400 into the upper intervertebral space. Similarly, the alternate, lower, insertion plate 2700 is provided to facilitate a preferred simultaneous implantation of the upper and lower elements 2500,2600 of the alternate, lower, cervical disc replacement device 2400 into the lower intervertebral space. The upper and lower elements 1500,1600 are held by the insertion plate 1700 (preferably using mounting screws 1714a,1714b) in a preferred relationship to one another that is suitable for implantation, identical to the preferred relationship in which the upper and lower elements 500,600 are held by the insertion plate 700 as described above. Similarly, the upper and lower elements 2500,2600 are held by the insertion plate 2700 (preferably using mounting screws 2714a,2714b) in a preferred relationship to one another that is suitable for implantation, identical to the preferred relationship in which the upper and lower elements 500,600 are held by the insertion plate 700 as described above.

The illustrated alternate, upper, insertion plate 1700 is identical in structure to the insertion plate 700 described above (and thus like components are like numbered, but in the 1700s rather than the 700s), with the exception that the lower flange 1704b is offset from the midline (to the right in an anterior view) to align its mounting screw hole 1712b with the offset mounting screw hole 1609 of the alternate lower element 1600 of the alternate, upper, cervical disc replacement device 1400. Similarly, the illustrated alternate, lower, insertion plate 2700 is identical in structure to the insertion plate 700 described above (and thus like components are like numbered, but in the 2700s rather than the 700s), with the exception that the upper flange 2704a is offset from the midline (to the left in an anterior view) to align its mounting screw hole 2712a with the offset mounting screw hole 2509 of the alternate upper element 2500 of the alternate, lower, cervical disc replacement device 2400.

Accordingly, the upper and lower elements 1500,1600, being held by the insertion plate 1700, as well as the upper and lower elements 2500,2600, being held by the insertion plate 2700, can be implanted using the insertion handle 800, insertion pusher 900, drill guide 1000, clips 1150a,1150b (one on the upper element flange 1506, and one on the lower element flange 2606, because only the upper element 1500 and the lower element 2600 are secured by bone screws), and clip applicator 1100, in the manner described above with respect to the implantation of the cervical disc replacement device 400.

It should be noted that the described alternate configuration (that includes two cervical disc replacement devices) presents the cervical disc replacement devices to the surgeon in a familiar manner. That is, by way of explanation, current cervical fusion surgery involves placing a fusion device (e.g., bone or a porous cage) in between the upper and middle cervical intervertebral bones, and in between the middle and lower vertebral bones, and attaching an elongated two-level cervical fusion plate to the anterior aspects of the bones. Widely used two-level cervical fusion devices (an example two level fusion plate 1350 is shown in anterior view in FIG. 13c and in lateral view in FIG. 13d) are configured with a pair of laterally spaced bone screw holes 1352a,1352b on an upper end 1354 of the plate 1350, a pair of laterally spaced bone screw holes 1356a,1356b on a lower end 1358 of the plate 1350, and a pair of laterally spaced bone screw holes 1360a,1360b midway between the upper and lower ends 1354,1358. To attach the plate 1350 to the bones, bone screws are disposed through the bone screw holes and into the corresponding bones. This prevents the bones from moving relative to one another, and allows the bones to fuse to one another with the aid of the fusion device.

Figure 14A:
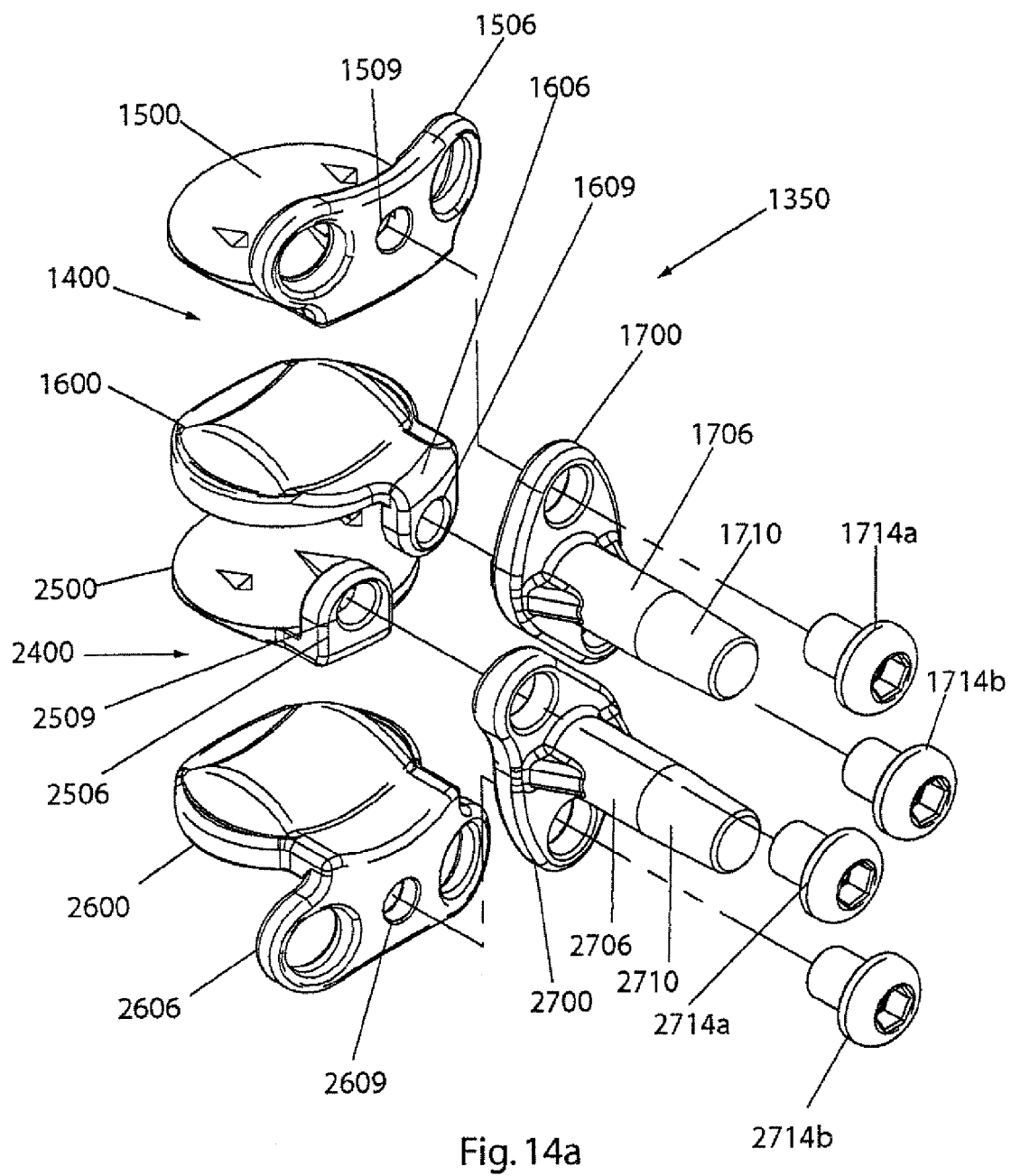
FIGS. 14a-e show an alternate, dual cervical disc replacement device configuration and alternate insertion plates for use therewith, in exploded perspective (FIG. 14a), anterior (FIG. 14b), posterior (FIG. 14c), lateral (FIG. 14d), and collapsed perspective (FIG. 14e) views.
Figure 14B:
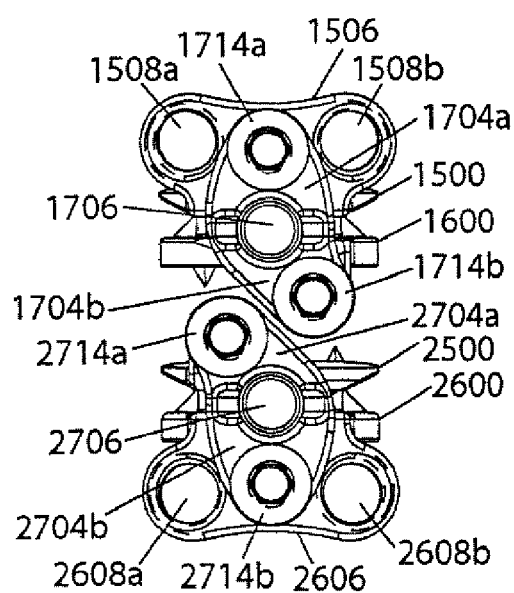
Figure 14C:
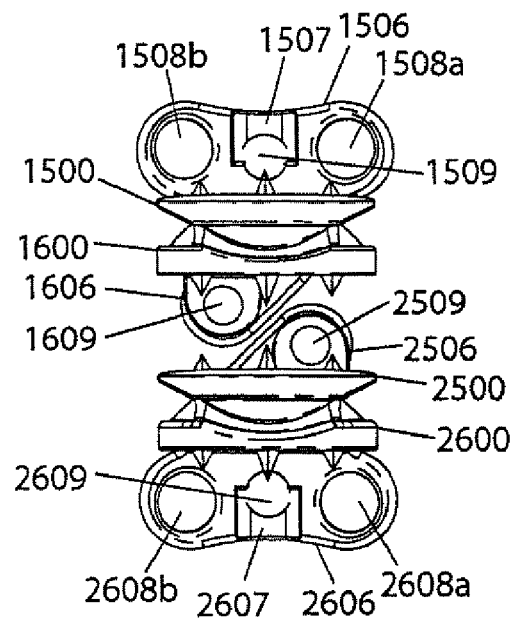
Figure 14D:
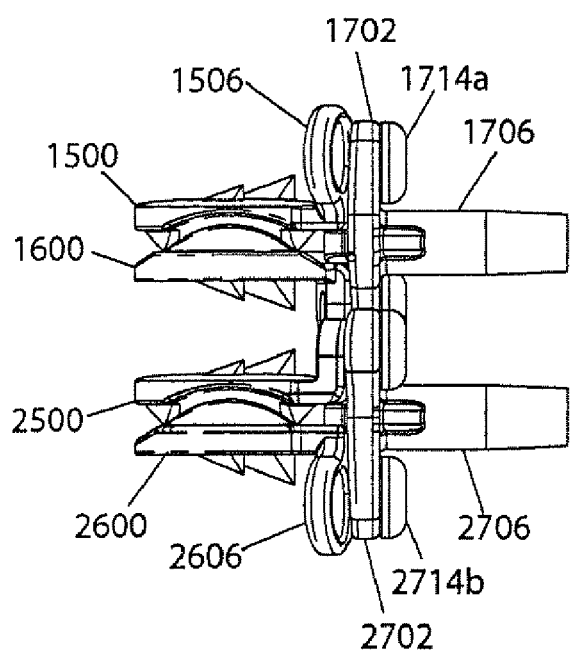
Figure 14E:
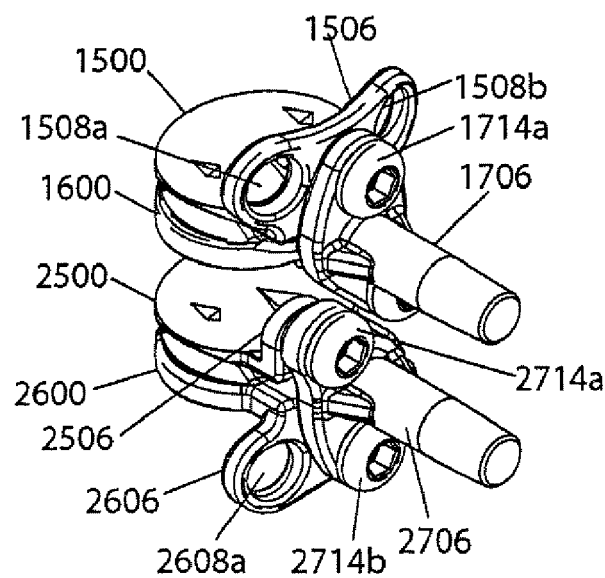

Accordingly, as can be seen in FIG. 14b, when the upper and lower elements 1500,1600 of the cervical disc replacement device 1400, and the upper and lower elements 2500, 2600 of the cervical disc replacement device 2400, are held in the preferred spatial relationship and aligned for implantation, the upper element flange 1506 and lower element flange 2606, and their bone screw holes 1508a,1508b and 2608a, 2608b, present to the surgeon a cervical hardware and bone screw hole configuration similar to a familiar two level cervical fusion plate configuration (as described above, a middle pair of bone screws holes is not needed; however, middle bone screw holes are contemplated by the present invention for some embodiments, if necessary or desirable). The mounting of the elements 1500,1600 to the insertion plate 1700 allows the elements 1500,1600 to be manipulated as a single unit for implantation (by manipulating the insertion plate 1700), similar to the way a cervical fusion plate is manipulatable as a single unit for attachment to the bones. Similarly, the mounting of the elements 2500,2600 to the insertion plate 2700 allows the elements 2500,2600 to be manipulated as a single unit for implantation (by manipulating the insertion plate 2700), similar to the way a cervical fusion plate is manipulatable as a single unit for attachment to the bones. This aspect of the present invention simplifies and streamlines the cervical disc replacement device implantation procedure.

While there has been described and illustrated specific embodiments of cervical disc replacement devices and insertion instrumentation, it will be apparent to those skilled in the art that variations and modifications are possible without deviating from the broad spirit and principle of the invention. The invention, therefore, shall not be limited to the specific embodiments discussed herein.

The invention claimed is:

1. A method for replacing at least a portion of an intervertebral disc in a spinal column, comprising the steps of:
removing the portion of the intervertebral disc from the spinal column; and
inserting first and second members of an intervertebral disc replacement device into an intervertebral disc space of the spinal column, the first and second members being detachably engaged with an insertion plate operable to substantially maintain the first and second members in registration with one another;

providing a drill guide including a shaft having a proximal end and a distal end, and a guide member disposed at the distal end of the shaft for engaging with the insertion plate;

inserting a portion of the drill guide over a first alignment element on the insertion plate;

inserting a drill bit through at least one guide bore of the guide member to align the drill bit with an area of a vertebral bone of the intervertebral disc space to which one of the first and second members of the intervertebral disc replacement device is to be attached; and drilling the vertebral bone.

2. The method of claim 1, further comprising the step of using the drill guide to urge the first and second members of the intervertebral disc replacement device into a target position within the intervertebral disc space before drilling the vertebral bone.

3. The method of claim 1, further comprising the steps of:
orienting the guide member into a first alignment mode with respect to the insertion plate such that the at least one guide bore aligns with an area of a first vertebral bone of the intervertebral disc space to which the first member of the intervertebral disc replacement device is to be attached;

drilling the first vertebral bone;

orienting the guide member into a second alignment mode with respect to the insertion plate such that the at least one guide bore aligns with an area of a second vertebral bone of the intervertebral disc space to which the second member of the intervertebral disc replacement device is to be attached; and drilling the second vertebral bone.

4. The method of claim 3, further comprising the step of fixing the first member of the intervertebral disc replacement device to the first vertebral bone prior to drilling the second vertebral bone.

5. The method of claim 3, wherein:
the guide member includes a second alignment element operable to variably engage the first alignment element on the insertion plate to achieve the first and second alignment modes;

the first member of the intervertebral disc replacement device includes a first vertebral contact surface and a first flange including at least one through hole for receiving a bone screw for fastening the first member to the first vertebral bone of the spinal column; and the method further comprises (1) engaging at least a third alignment element on the guide member with the at least one through hole of the first flange when the first alignment element engages the second alignment element in the first alignment mode, and (ii) drilling the first vertebral bone.

6. The method of claim 5, wherein:
the second member of the intervertebral disc replacement device includes a second vertebral contact surface and a second flange including at least one through hole for receiving a bone screw for fastening the second member to the second vertebral bone of the spinal column; and the method further comprises (i) variably engaging the first alignment element and the second alignment element to achieve the second alignment mode, (ii) engaging at least the third alignment element on the guide member with the at least one through hole of the second flange, and (iii) drilling the second vertebral bone.

7. A method for performing spinal surgery comprising the steps of:
removably attaching an intervertebral disc replacement device including a first member having a first articulation surface and a second member having a second articulation surface to an insertion plate;

removably attaching a shaft with the insertion plate by engaging a first alignment element on the insertion plate with a second alignment element on the shaft;

manipulating the shaft to insert the intervertebral disc replacement device between first and second vertebral bodies;

removing the shaft from the insertion plate;

attaching a drill guide to the insertion plate;

drilling the first and second vertebral bodies by guiding a drill bit with the drill guide; and removing the drill guide.

8. The method of claim 7, further comprising the steps of affixing the first member to the first vertebral body and the second member to the second vertebral body.

9. The method of claim 8, further comprising the step of removing the insertion plate.

10. The method of claim 7, wherein the attaching step includes attaching the drill guide in a first orientation so as to allow drilling of the first vertebral body and in a second orientation so as to allow drilling of the second vertebral body.

11. The method of claim 10, wherein the drilling step includes drilling two holes in each of the first and second vertebral bodies.

12. The method of claim 7, wherein the drill guide includes a third alignment element, the second and third alignment elements being engageable with the first alignment element.

13. The method of claim 12, wherein the first alignment element is a stem and the second and third alignment elements are bores.

14. The method of claim 7, wherein the first and second members each include flanges and the removably attaching step includes affixing the insertion plate to the flange through the use of screws.

15. The method of claim 14, wherein the flanges include at least one bone screw hole operable to receive bone screws for affixing the first and second members to one of the first and second vertebral bodies and at least one mounting screw hole operable for receiving the screws to affix the insertion plate to the first and second members.

16. The method of claim 15, wherein the insertion plate includes a perimeter that does not extend over the bone screw holes of the first and second flanges.

17. A method for performing spinal surgery comprising the steps of:
removably attaching an intervertebral disc replacement device including a first member having a first articulation surface and a second member having a second articulation surface to an insertion plate, the insertion plate maintaining the first and second articulation surfaces in registration with one another;

removably attaching a shaft with the insertion plate;

manipulating the shaft to insert the intervertebral disc replacement device between first and second vertebral bodies;

removing the shaft from the insertion plate;

attaching a drill guide to the insertion plate in a first orientation and drilling the first vertebral body by guiding a drill bit with the drill guide;

attaching a drill guide to the insertion plate in a second orientation and drilling the second vertebral body by guiding a drill bit with the drill guide;

removing the drill guide; and affixing the first member to the first vertebral body and the second member to the second vertebral body, wherein the insertion plate includes a first alignment element, the shaft includes a second alignment element, and the drill guide includes a third alignment element, the second and third alignment elements being engageable with the first alignment element.

18. The method of claim 17, wherein the attaching and drilling step includes drilling two holes in each of the first and second vertebral bodies.

19. The method of claim 17, wherein the first alignment element is a stem and the second and third alignment elements are bores.

20. The method of claim 17, wherein the first and second members each include flanges including at least one bone screw hole operable to receive bone screws for affixing the first and second members to one of the first and second vertebral bodies and at least one mounting screw hole operable for receiving the screws to affix the insertion plate to the first and second members, and the insertion plate includes a perimeter that does not extend over the bone screw holes of the first and second flanges.

* * * * *

UNITED STATES PATENT AND TRADEMARK OFFICE
CERTIFICATE OF CORRECTION

PATENT NO. : 8,109,979 B2  
APPLICATION NO. : 12/634182  
DATED : February 7, 2012  
INVENTOR(S) : Rafail Zubok, Michael W. Dudasik and Joseph P. Errico Page 1 of 1

It is certified that error appears in the above-identified patent and that said Letters Patent is hereby corrected as shown below:

On the Title page, item 74, "Krumholtz" should read -- Krumholz --.

Signed and Sealed this
Eighteenth Day of August, 2015

Michelle K. Lee
*Director of the United States Patent and Trademark Office*